US010744193B2

(12) United States Patent
Khurana et al.

(10) Patent No.: US 10,744,193 B2
(45) Date of Patent: Aug. 18, 2020

(54) IMMUNOGENIC RSV POLYPEPTIDES

(71) Applicant: The United States of America, as represented by the Secretary, Department of Health and Human Services, Silver Spring, MD (US)

(72) Inventors: Surender Khurana, Clarksburg, MD (US); Hana Golding, Rockville, MD (US)

(73) Assignee: The United States of America, as represented by the Secretary, Department of Health and Human Services, Silver Spring, MD (US)

( * ) Notice: Subject to any disclaimer, the term of this patent is extended or adjusted under 35 U.S.C. 154(b) by 0 days.

(21) Appl. No.: 15/562,862

(22) PCT Filed: Feb. 18, 2016

(86) PCT No.: PCT/US2016/018530
§ 371 (c)(1),
(2) Date: Sep. 28, 2017

(87) PCT Pub. No.: WO2016/160166
PCT Pub. Date: Oct. 6, 2016

(65) Prior Publication Data
US 2018/0110850 A1 Apr. 26, 2018

Related U.S. Application Data

(60) Provisional application No. 62/139,995, filed on Mar. 30, 2015.

(51) Int. Cl.
| *A61K 39/12* | (2006.01) |
| *C07K 14/135* | (2006.01) |
| *A61P 31/14* | (2006.01) |
| *C12N 7/00* | (2006.01) |
| *G01N 33/569* | (2006.01) |
| *A61K 39/00* | (2006.01) |

(52) U.S. Cl.
CPC .............. *A61K 39/12* (2013.01); *A61P 31/14* (2018.01); *C12N 7/00* (2013.01); *G01N 33/56983* (2013.01); *A61K 2039/523* (2013.01); *A61K 2039/54* (2013.01); *A61K 2039/55* (2013.01); *A61K 2039/555* (2013.01); *A61K 2039/55566* (2013.01); *A61K 2039/645* (2013.01); *C12N 2760/18534* (2013.01); *C12N 2760/18571* (2013.01)

(58) Field of Classification Search
None
See application file for complete search history.

(56) References Cited

U.S. PATENT DOCUMENTS 7,309,494 B2 * 12/2007 Corvaia ............... A61K 39/155
424/211.1
9,303,082 B2 * 4/2016 Mueller ................. A61K 39/12

FOREIGN PATENT DOCUMENTS

| WO | WO 2011/091279 | 7/2011 |
| WO | WO 2014/079842 | 5/2014 |
| WO | WO 2014/140190 | 9/2014 |
| WO | WO 2014/144756 | 9/2014 |
| WO | WO 2014/174018 | 10/2014 |

OTHER PUBLICATIONS

Levely et al. Immunodominant T-Cell Epitope on the F Protein of Respiratory Syncytial Virus Recognized by Human Lymphocytes. J Virol. Jul. 1991;65(7):3789-96.*
Quan et al. Viruslike Particle Vaccine Induces Protection Against Respiratory Syncytial Virus Infection in Mice. The Journal of Infectious Diseases 2011;204:987-95.*
GenBank AIZ95496.1. attachment glycoprotein [Human orthopneumovirus]. Dated Dec. 21, 2014.*
Shingai et al. Soluble G protein of respiratory syncytial virus inhibits Toll-like receptor 3/4-mediated IFN-beta induction. International Immunology, 2008, vol. 20, No. 9, pp. 1169-1180.*
Mader et al. Liposome encapsulation of a soluble recombinant fragment of the respiratory syncytial virus (RSV) G protein enhances immune protection and reduces lung eosinophilia associated with virus challenge. Vaccine 18 (2000) 1110-1117.*
Seitz et al. Influence of Oxidation and Multimerization on the Immunogenicity of a Thioredoxin-L2 Prophylactic Papillomavirus Vaccine. Clinical and Vaccine Immunology, 2013, 20: 1061-1069.*
Murata et al. Identification of and Human Serum Reactogenicity to Neutralizing Epitopes within the Central Unglycosylated Region of the Respiratory Syncytial Virus Attachment Protein. Clinical and Vaccine Immunology, Apr. 2010, 17(4): 695-697.*
Anderson, et al. "Identification of epitopes on respiratory syncytial virus proteins by competitive binding immunoassay." *Journal of Clinical Microbiology* 23, No. 3 (1986): 475-480.
Anderson, et al. "Neutralization of respiratory syncytial virus by individual and mixtures of F and G protein monoclonal antibodies." *Journal of Virology* 62, No. 11 (1988): 4232-4238.
Castilow, et al. "IL-13 is required for eosinophil entry into the lung during respiratory syncytial virus vaccine-enhanced disease," *The Journal of Immunology* 180, No. 4 (2008): 2376-2384.
Choi, et al. "Antibodies to the central conserved region of respiratory syncytial virus (RSV) G protein block RSV G protein CX3C-CX3CR1 binding and cross-neutralize RSV A and B strains," *Viral Immunology* 25, No. 3 (2012): 193-203.

(Continued)

*Primary Examiner* — Nianxiang Zou
(74) *Attorney, Agent, or Firm* — Klarquist Sparkman, LLP

(57) ABSTRACT

This invention provides immunogenic compositions comprising an immune stimulant and an respiratory syncytial virus (RSV) oligopeptide or an unglycosylated RSV polypeptide. The RSV oligopeptides are shown in SEQ ID NO: 3-33. The unglycosylated RSV polypeptide may consist essentially of the ectodomain of an RSV G protein, such as that shown in SEQ ID NO: 2 or the ectodomain of an RSV F protein such as the ectodomain of the F protein shown in SEQ ID NO: 39.

7 Claims, 8 Drawing Sheets
Specification includes a Sequence Listing.

(56) References Cited

OTHER PUBLICATIONS

Connors, et al. "Pulmonary histopathology induced by respiratory syncytial virus (RSV) challenge of formalin-inactivated RSV-immunized. BALB/c mice is abrogated by depletion of CD4+ T cells." *Journal of Virology* 66, No. 12 (1992): 7444-7451.

Corvaïa, et al. "Challenge of BALB/c mice with respiratory syncytial virus does not enhance the Th2 pathway induced after immunization with a recombinant G fusion protein, BBG2NA, in aluminum hydroxide." *Journal of Infectious Diseases* 176, No. 3 (1997): 560-569.

De Graaff, et al. "HLA-DP4 presents an immunodominant peptide from the RSV G protein to CD4 T cells." *Virology* 326, No. 2 (2004): 220-230.

De Waal, et al. "Evaluation of BBG2Na in infant macaques: specific immune responses after vaccination and RSV challenge." *Vaccine* 22, No. 8 (2004): 915-922.

Everard, et al. "Analysis of cells obtained by bronchial lavage of infants with respiratory syncytial virus infection." *Archives of Disease in Childhood* 71, No. 5 (1994): 428-432.

Fuentes, et al. "Development of a simple, rapid, sensitive, high-throughput luciferase reporter based microneutralization test for measurement of virus neutralizing antibodies following Respiratory Syncytial Virus vaccination and infection." *Vaccine* 31, No. 37 (2013): 3987-3994.

Graham, Barney S. "Biological challenges and technological opportunities for respiratory syncytial virus vaccine development." *Immunological Reviews* 239, No. 1 (2011): 149-166.

Hancock, et al. "Generation of atypical pulmonary inflammatory responses in BALB/c mice after immunization with the native attachment (G) glycoprotein of respiratory syncytial virus." *Journal of Virology* 70, No. 11 (1996): 7783-7791.

Haynes, et al. "Enhanced disease and pulmonary eosinophilia associated with formalin-inactivated respiratory syncytial virus vaccination are linked to G glycoprotein CX3C-CX3CR1 interaction and expression of substance P." *Journal of Virology* 77, No. 18 (2003): 9831-9844.

Hertz, et al. "Respiratory syncytial virus-induced acute lung injury in adult patients with bone marrow transplants: a clinical approach and review of the literature." *Medicine* 68, No. 5 (1989): 269-281.

Jafri, et al. "Respiratory syncytial virus induces pneumonia, cytokine response, airway obstruction, and chronic inflammatory infiltrates associated with long-term airway hyperresponsiveness in mice," *Journal of Infectious Diseases* 189, No. 10 (2004): 1856-1865.

Johnson, et al. "Secreted respiratory syncytial virus G glycoprotein induces interleukin-5 (IL-5), IL-13, and eosinophilia by an IL-4-independent mechanism." *Journal of Virology* 73, No. 10 (1999): 8485-8495.

Johnson, et al. "Respiratory syncytial virus glycoprotein G interacts with DC-SIGN and L-SIGN to activate ERK1 and ERK2." *Journal of Virology* 86, no. 3 (2012): 1339-1347.

Johnson, et al. "Priming with secreted glycoprotein G of respiratory syncytial virus (RSV) augments interleukin-5 production and tissue eosinophilia after RSV challenge." *Journal of Virology* 72, No. 4 (1998): 2871-2880.

Jorquera, et al. "Nanoparticle vaccines encompassing the respiratory syncytial virus (RSV) G protein CX3C chemokine motif induce robust immunity protecting from challenge and disease." *PloS one* 8, No. 9 (2013): e74905.

Karron, et al. "Identification of a recombinant live attenuated respiratory syncytial virus vaccine candidate that is highly attenuated in infants." *The Journal of Infectious Diseases* 191, No. 7 (2005): 1093-1104.

Khurana, et al. "Recombinant HA1 produced in *E. coli* forms functional oligomers and generates strain-specific SRID potency antibodies for pandemic influenza vaccines." *Vaccine* 29, No. 34 (2011): 5657-5665.

Khurana, et al. "Bacterial HA1 vaccine against pandemic H5N1 influenza virus: evidence of oligomerization, hemagglutination, and cross-protective immunity in ferrets." *Journal of Virology* 85, No. 3 (2011): 1246-1256.

Khurana., et al. "Properly folded bacterially expressed H1N1 hemagglutinin globular head and ectodomain vaccines protect ferrets against H1N1 pandemic influenza virus." *PLoS One* 5, No. 7 (2010): e11548.

Lee, et al. "Baculovirus-expressed virus-like particle vaccine in combination with DNA encoding the fusion protein confers protection against respiratory syncytial virus." *Vaccine* 32, No. 44 (2014): 5866-5874.

Lu, et al. "A rapid Flp-In system for expression of secreted H5N1 influenza hemagglutinin vaccine immunogen in mammalian cells." *PLoS One* 6, No. 2 (2011): e17297.

McLellan, et al. "Structure of RSV fusion glycoprotein trimer bound to a prefusion-specific neutralizing antibody." *Science* 340, No. 6136 (2013): 1113-1117.

Murphy, et al. "Dissociation between serum neutralizing and glycoprotein antibody responses of infants and children who received inactivated respiratory syncytial virus vaccine." *Journal of Clinical Microbiology* 24, No. 2 (1986): 197-202.

Murphy, et al. "Formalin-inactivated respiratory syncytial virus vaccine induces antibodies to the fusion glycoprotein that are deficient in fusion-inhibiting activity." *Journal of Clinical Microbiology* 26, No. 8 (1988): 1595-1597.

Ofek, et al. "Elicitation of structure-specific antibodies by epitope scaffolds." *Proceedings of the National Academy of Sciences* 107, No. 42 (2010): 17880-17887.

Olson, et al. "CD8 T cells inhibit respiratory syncytial virus (RSV) vaccine-enhanced disease." *The Journal of Immunology* 179, No. 8 (2007): 5415-5424.

Olson, et al. "The number of respiratory syncytial virus (RSV)-specific memory CD8 T cells in the lung is critical for their ability to inhibit RSV vaccine-enhanced pulmonary eosinophilia." *The Journal of Immunology* 181, No. 11 (2008): 7958-7968.

Plotnicky-Gilquin, et al. "Absence of lung immunopathology following respiratory syncytial virus (RSV) challenge in mice immunized with a recombinant RSV G protein fragment" *Virology* 258, No. 1 (1999): 128-140.

Polack, et al. "A role for immune complexes in enhanced respiratory syncytial virus disease." *Journal of Experimental Medicine* 196, No. 6 (2002): 859-865.

Power, et al. "The immunogenicity, protective efficacy and safety of BBG2Na, a subunit respiratory syncytial virus (RSV) vaccine candidate, against RSV-B." *Vaccine* 22, No. 2 (2003): 168-176.

Power, et al. "Induction of protective immunity in rodents by vaccination with a prokaryotically expressed recombinant fusion protein containing a respiratory syncytial virus G protein fragment." *Virology* 230, No. 2 (1997): 155-166.

Power, et al. "Safety and immunogenicity of a novel recombinant subunit respiratory syncytial virus vaccine (BBG2Na) in healthy young adults." *The Journal of Infectious Diseases* 184, No. 11 (2001): 1456-1460.

Raghunandan, et al. "An insect cell derived respiratory syncytial virus (RSV) F nanoparticle vaccine induces antigenic site II antibodies and protects against RSV challenge in cotton rats by active and passive immunization." *Vaccine* 32, No. 48 (2014): 6485-6492.

Rissoan, et al. "Reciprocal control of T helper cell and dendritic cell differentiation." *Science* 283, No. 5405 (1999): 1183-1186.

Satake, et al. "Respiratory syncytial virus envelope glycoprotein (G) has a novel structure." *Nucleic Acids Research* 13, No. 21 (1985): 7795-7812.

Srikiatkhachorn, et al. "Virus-specific memory and effector T lymphocytes exhibit different cytokine responses to antigens during experimental murine respiratory syncytial virus infection." *Journal of Virology* 71, No. 1 (1997): 678-685.

Subbaryan et al. "Expression and characterization of a multivalent human respiratory syncytial virus protein." *Molecular Biology* 44, No. 3 (2010): 477-487.

Swanson, et al. "A monomeric uncleaved respiratory syncytial virus F antigen retains prefusion-specific neutralizing epitopes." *Journal of Virology* 88, No. 20 (2014): 11802-11810.

Thompson, et al. "Mortality associated with influenza and respiratory syncytial virus in the United States." *Jama* 289, No. 2 (2003): 179-186.

(56) References Cited

OTHER PUBLICATIONS

Tripp, et al. "Respiratory syncytial virus infection and G and/or SH protein expression contribute to substance P, which mediates inflammation and enhanced pulmonary disease in BALB/c mice." *Journal of Virology* 74, No. 4 (2000): 1614-1622.
Tripp, et al. "Respiratory syncytial virus G and/or SH protein alters Th1 cytokines, natural killer cells, and neutrophils responding to pulmonary infection in BALB/c mice." *Journal of Virology* 73, No. 9 (1999): 7099-7107.
Verma, et al. "Oligomeric recombinant H5 HA1 vaccine produced in bacteria protects ferrets from homologous and heterologous wild-type H5N1 influenza challenge and controls viral loads better than subunit H5N1 vaccine by eliciting high-affinity antibodies." *Journal of Virology* 86, No. 22 (2012): 12283-12293.
Zhou, et al. "Hospitalizations associated with influenza and respiratory syncytial virus in the United States, 1993-2008." *Clinical Infectious Diseases* 54, No. 10 (2012): 1427-1436.
Lee et al., "Protective antigenic sites in respiratory syncytial virus G attachment protein outside the central conserved and cysteine noose domains." *PLoS Pathog* No. 8 (2018): 1-22.

\* cited by examiner

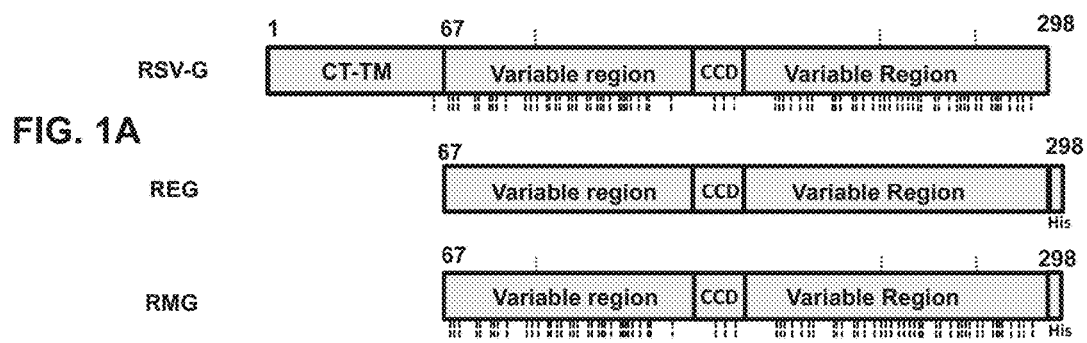
FIG. 1A
FIG. 1B
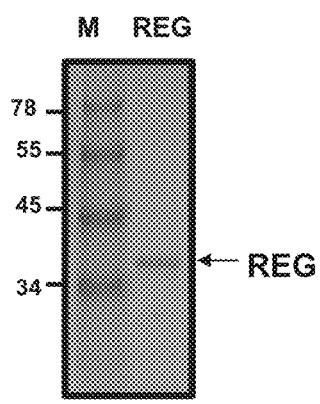
FIG. 1C
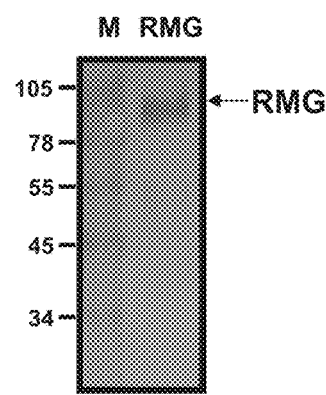
FIG. 1D
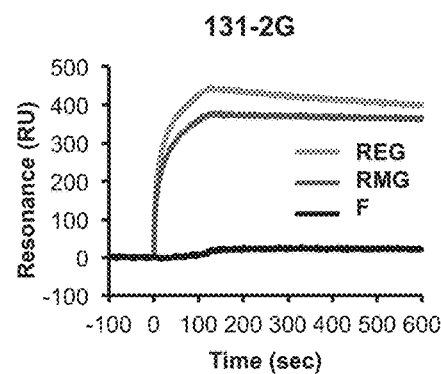
FIG. 1E
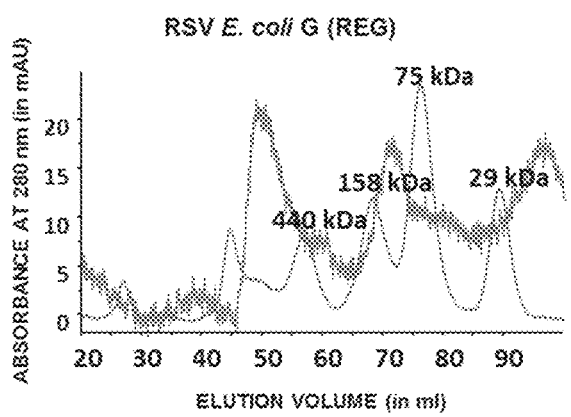
FIG. 1F
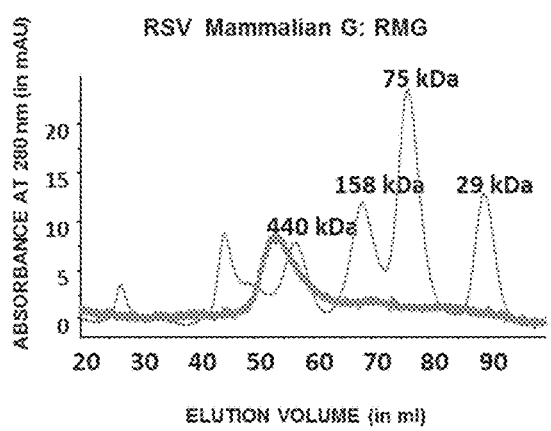

| Group | Dose | Virus Challenge | N |
|---|---|---|---|
| PBS | - | RSV A2 | 9 |
|  |  | RSV B1 | 9 |
| RSV A2 G E. Coli (REG) | 5 ug | RSV A2 | 11 |
|  |  | RSV B1 | 11 |
| RSV A2 G Mammalian (RMG) | 5 ug | RSV A2 | 11 |
|  |  | RSV B1 | 11 |
| RSV A2 F | 5 ug | RSV A2 | 6 |
|  |  | RSV B1 | 6 |

FIG. 4A  Total binding to REG in SPR
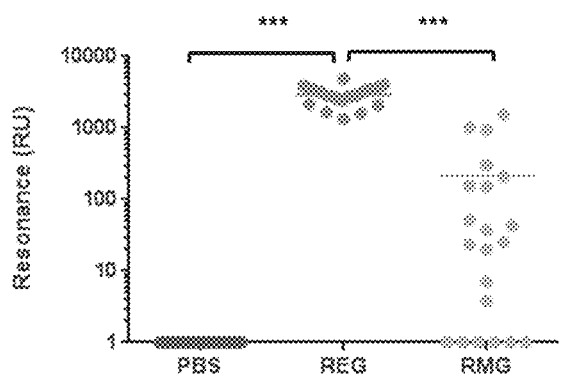
FIG. 4B  Total binding to RMG in SPR
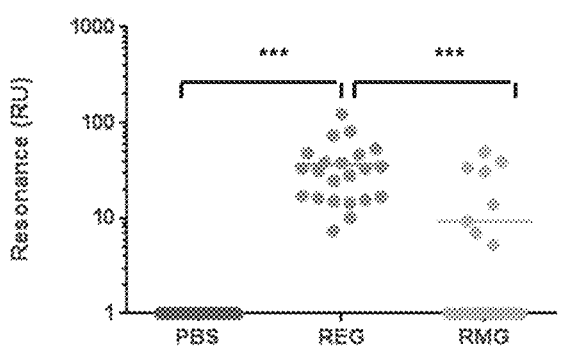
FIG. 4C
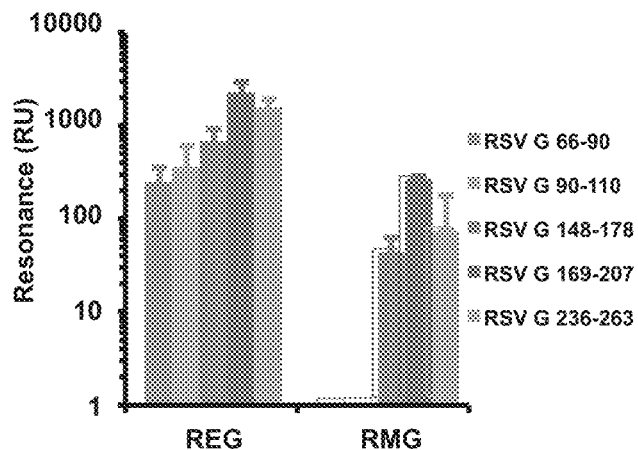

FIG. 5A RSV A2
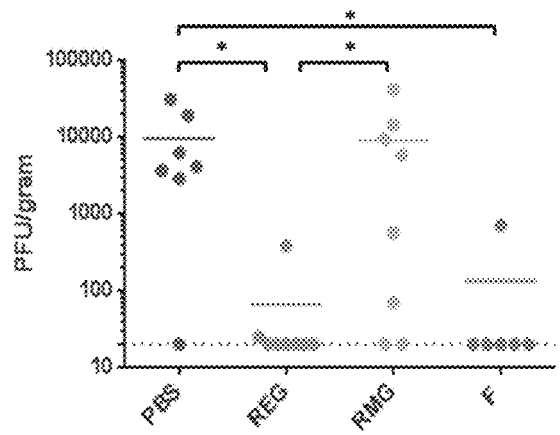
FIG. 5B RSV B1
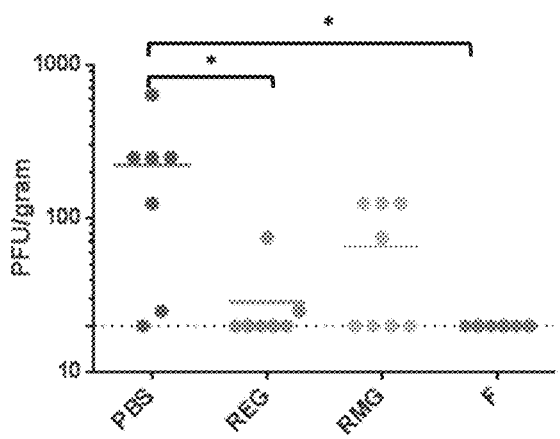
FIG. 5C
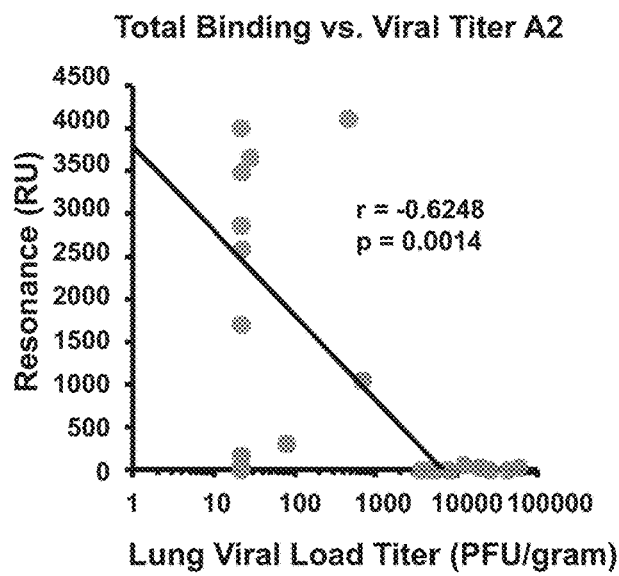

| | Immunization | PRNT titers | Lung Pathology Scores | | | |
|---|---|---|---|---|---|---|
| | | | Peribronchiolitis | Perivasculitis | Interstitial Pneumonia | Total 12 max |
| RSV A2 | PBS | <40 | 1 | 0.8 | 1 | 2.8 |
| | REG | 503 - 1198 | 0.5 | 0.8 | 0.5 | 1.8 |
| | RMG | <40 | 1.3 | 1.8 | 1.8 | 4.9 |
| RSV B1 | PBS | <40 | 0 | 1.3 | 1 | 2.3 |
| | REG | <40 | 0 | 0.7 | 0 | 0.7 |
| | RMG | <40 | 1 | 1.7 | 1.2 | 3.9 |

PBS     REG     RMG

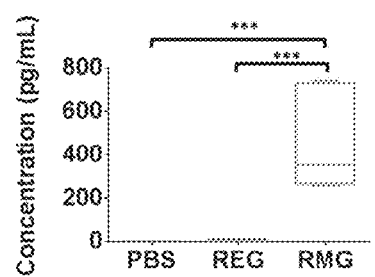
FIG. 7A IL-4
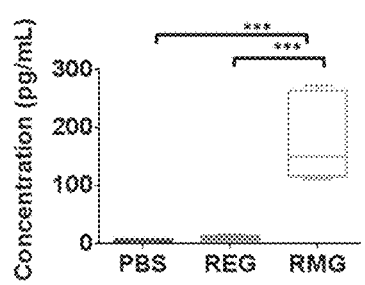
FIG. 7B IL-5
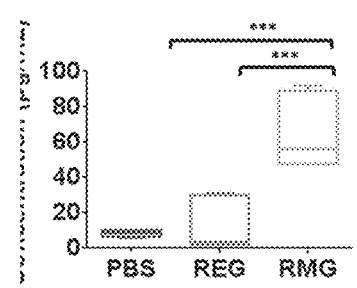
FIG. 7C IL-6
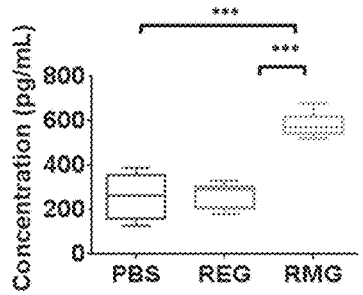
FIG. 7D IL-13
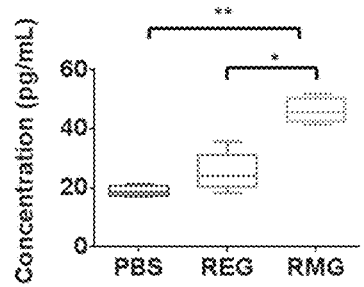
FIG. 7E IFN-γ
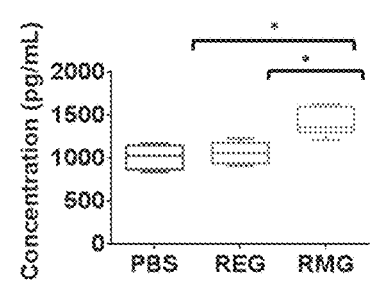
FIG. 7F Eotaxin
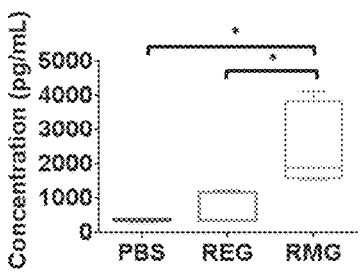
FIG. 7G MCP-1
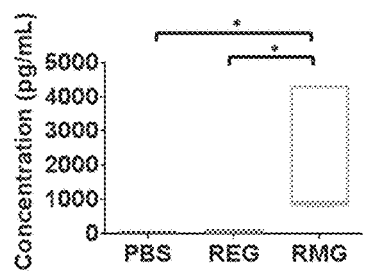
FIG. 7H MIP-1α
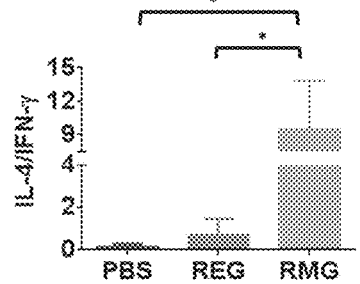
FIG. 7I Th2/Th1 ratio

```
                            1                                                  50
RSV_A_ST_A2       (1)   MSKNKDQRTAKTLERTWDTLNHLLFISSCLYKLNLKSVAQITLSILAMII
RSV_A_ST_LONG     (1)   MSKNKDQRTAKTLEKTWDTLNHLLFISSGLYKLNLKSIAQITLSILAMII
RSV_B_ST_18537    (1)   MSKHKNQRTARTLEKTWDTLNHLIVISSCLYKLNLKSIAQIALSVLAMII
RSV_B_ST_B1       (1)   MSKHKNQRTARTLEKTWDTLNHLIVISSCLYKLNLKSIAQIALSVLAMII 51                                                 100
RSV_A_ST_A2      (51)   STSLIIAAIIFIASANHKVTPTTAIIQDATSQIKNTTPTYLTQNPQLGIS
RSV_A_ST_LONG    (51)   STSLIITAIIFIASANHKVTLTTAIIQDATSQIKNTTPTYLTQDPQLGIS
RSV_B_ST_18537   (51)   STSLIIAAIIFIISANHKVTLTTVTVQTIKNHTEKNISTYLTQVPPERVN
RSV_B_ST_B1      (51)   STSLIIAAIIFIISANHKVTLTTVTVQTIKNHTEKNITTYLTQVPPERVS 101                                                150
RSV_A_ST_A2     (101)   PSNPSEITSQITTILASTTPGVKSTLQSTTVKTKNTTTTQTQPSKPTTKQ
RSV_A_ST_LONG   (101)   FSNLSEITSQTTTILASTTPGVKSNLQPTTVKTKNTTTTQTQPSKPTTKQ
RSV_B_ST_18537  (101)   SSKQPTTTSPIHTNSATISPNTKSETHHTTAQTKGRITTSTQTNKPSTKS
RSV_B_ST_B1     (101)   SSKQPTTTSPIHTNSATTSPNTKSETHHTTAQTKGRTTTSTQTNKPSTKP 151                                                200
RSV_A_ST_A2     (151)   RQNKPPSKPNNDFHFEVFNFVPCSICSNNPTCWAICKRIPNKKPGKKTT
RSV_A_ST_LONG   (151)   RQNKPPNKPNNDFHFEVFNFVPCSICSNNPTCWAICKRIPNKKPGKKTT
RSV_B_ST_18537  (151)   RSKNPPKKPKDDYHFEVFNFVPCSICGNNQLCKSICKTIPSNKPKKKPTI
RSV_B_ST_B1     (151)   RLKNPPKKPKDDYHFEVFNFVPCSICGNNQLCKSICKTIPSNKPKKKPTI 201                                                250
RSV_A_ST_A2     (201)   KPTKKPTLKTT-KKDPKPQTTKSKEVPTTKPTEEPTINTTKTNIITTLLT
RSV_A_ST_LONG   (201)   KPTKKPTFKTT-KKDHKPQTTKPKEVPTTKPTEEPTINTTKTNIITTLLT
RSV_B_ST_18537  (201)   KPTNKPTTKTTNKRDPKTPAKMPKKETITNPAKKPTLKTTERDTSISQST
RSV_B_ST_B1     (201)   KPTNKPTTKTTNKRDPKTPAKTTKKETTTNPTKKPTLTTTERDTSTSQST 251                                                299
RSV_A_ST_A2     (250)   SNTTGNPELTSQMETFHSTSSEGNPSPSQVSTTSEYPSQPSSPPNTPRQ
RSV_A_ST_LONG   (250)   NNTTGNPKLTSQMETFHSTSSEGNLSPSQVSTTSEHPSQPSSPPNTPRQ
RSV_B_ST_18537  (251)   VLDTITPKYTIQQQSLHSTSSENTPSSTQIPTASEPSTLNPN-------
RSV_B_ST_B1     (251)   VLDTTTLEHTIQQQSLHSTTPENTPNSTQTPTASEPSTSNSTQNTQSHA
```

FIG. 8

IMMUNOGENIC RSV POLYPEPTIDES

CROSS REFERENCES TO RELATED APPLICATIONS

This is the U.S. National Stage of International Application No. PCT/US2016/018530, filed Feb. 18, 2016, which was published in English under PCT Article 21(2), which in turn claims the benefit of U.S. Provisional Application No. 62/139,995, filed Mar. 30, 2015, which is related to U.S. Application No. 61/910,623, filed Dec. 2, 2013, and International Application No. PCT/US14/68144, filed Dec. 2, 2014, all of which are incorporated herein by reference.

FIELD OF THE INVENTION

This invention relates to immunogenic polypeptides from human respiratory syncytial virus (RSV) and their use to prevent, treat and diagnose RSV infection.

BACKGROUND OF THE INVENTION

Human respiratory syncytial virus (RSV) is the most important cause of virus mediated lower respiratory tract illness (LRI) in infants and children worldwide. In infants, ~2,345 per 100,000 hospitalizations are attributable to RSV infection in the United States annually and RSV is one of the leading causes of morbidity/mortality second only to influenza virus (1). Although traditionally regarded as a pediatric pathogen, RSV can cause life-threatening pulmonary disease in bone marrow transplant recipients and immunocompromised patients (2, 3). Most RSV mediated severe disease and mortality occurs in infants younger than 2 years (4). Among the elderly, RSV is also a common cause of severe respiratory infections that requires hospitalization (4).

Although the importance of RSV as a respiratory pathogen has been recognized for over 50 years, a vaccine is not yet available because of several problems inherent in RSV vaccine development including the very young age of the target population, recurrent infections in spite of prior exposure, and history of enhanced disease in young children that were immunized with a formaldehyde inactivated RSV (FI-RSV) vaccine in the 1960s (3, 5). Subsequent studies with samples from these children showed poor functional antibody responses with low neutralization or fusion-inhibition titers (6, 7). There was also evidence for deposition of immune complexes in the small airways (8), however the mechanism of the FI-RSV vaccine induced enhanced disease is poorly understood. Animal models of the FI-RSV vaccine associated enhanced respiratory disease (VAERD) suggested a possible combination of poor functional antibody responses and Th2-biased hyper cytokine release leading to eosinophilic infiltration in the lungs (9, 10).

RSV live-attenuated vaccines (LAV) have a good safety record in infants. However, a recent RSV LAV candidate (rA2cp248/404/1030deltaSH) was found to be safe in infants but poorly immunogenic (11). New vaccine development efforts are now under way, using recombinant technologies, different cell substrates, and structure-based vaccine design (3). The RSV F glycoprotein (PFP-2) formulated in alum was evaluated in clinical trials and found to be well tolerated but only modestly immunogenic in adults, pregnant women, and in the elderly (12). A mixture of F, G, and M recombinant proteins was tested in subjects >65 years and was found to induce >4-fold increase in serum neutralizing activity in 58% of subjects with low pre-vaccine titers (13). Recently the structures of the F protective targets recognized by MAbs palivizumab and 101F, as well as the pre-fusion form of the F protein trimer were resolved, leading to structure based design of new F-based vaccines (14-16). A subunit vaccine based on the central conserved region of the G attachment surface glycoprotein was also developed as a RSV polypeptide with the albumin-binding domain from streptococcal protein G, produced in prokaryotic cells and formulated with an alum-based adjuvant. Despite promising results in murine models, challenge studies in rhesus macaques showed no reduction of viral loads, and studies in adults showed a relatively low capacity for inducing neutralizing antibodies (17, 18). An optimally effective RSV vaccine must protect against antigenically divergent groups A and B RSV strains.

Despite advances in the development of subunit vaccines, a need still exists to produce RSV vaccines that will provide protective immunity without the potential for disease enhancement. The present invention addresses these and other needs.

BRIEF SUMMARY OF THE INVENTION

This invention provides immunogenic compositions comprising an immune stimulant and an RSV oligopeptide from the RSV F protein or G protein or a multimer thereof. In other embodiments, the composition may comprise an unglycosylated. RSV polypeptide. Usually, the unglycosylated RSV polypeptide consists essentially of the ectodomain of an RSV G protein, such as one that is at least about 95% identical to that shown in SEQ ID NO: 2(RSV-A2) or SEQ ID NO: 42 (RSV-B1). Alternatively, the unglycosylated RSV polypeptide consists essentially of the ectodomain of an RSV F protein, such as one that is at least about 95% identical to the ectodomain of the F protein sequence shown in SEQ ID NO: 40. The unglycosylated RSV polypeptide can be made using a number of methods known in the art. In a typical embodiment, it is recombinantly expressed in a prokaryotic cell.

If the immunogenic composition comprises an RSV oligopeptide of the invention, the oligopeptide may be one or more of SEQ ID NO: 3-33. Thus, the composition of the invention may comprise SEQ ID NO: 3; alternatively, it may comprise SEQ ID NO: 4; alternatively, it may comprise SEQ ID NO: 5; alternatively, it may comprise SEQ II) NO: 6; alternatively, it may comprise SEQ ID NO: 7; alternatively, it may comprise SEQ ID NO: 8; alternatively, it may comprise SEQ ID NO: 9; alternatively, it may comprise SEQ II) NO: 10; alternatively, it may comprise SEQ ID NO: 11; alternatively, it may comprise SEQ ID NO: 12; alternatively, it may comprise SEQ ID NO: 13; alternatively, it may comprise SEQ ID NO: 14; alternatively, it may comprise SEQ ID NO: 15; alternatively, it may comprise SEQ ID NO: 16; alternatively, it may comprise SEQ ID NO: 17; alternatively, it may comprise SEQ ID NO: 18; alternatively, it may comprise SEQ ID NO: 19; alternatively, it may comprise SEQ ID NO: 20; alternatively, it may comprise SEQ ID NO: 21; alternatively, it may comprise SEQ ID NO: 22; alternatively, it may comprise SEQ ID NO: 23; alternatively, it may comprise SEQ ID NO: 24; alternatively, it may comprise SEQ ID NO: 25; alternatively, it may comprise SEQ ID NO: 26; alternatively, it may comprise SEQ ID NO: 27; alternatively, it may comprise SEQ ID NO: 28; alternatively, it may comprise SEQ ID NO: 29; alternatively, it may comprise SEQ ID NO: 30; alternatively, it may comprise SEQ ID NO: 31; alternatively, it may comprise SEQ ID NO: 32; alternatively, it may comprise or SEQ ID NO: 33.

The invention also provides methods of inducing a protective immune response against RSV infection in a subject. The methods comprise administering to the subject an immunologically effective amount of the immunogenic composition of the invention. Usually, the immunogenic composition is administered intramuscularly. The subject will typically be an infant, a pregnant mother, female of child bearing age, or an elderly person.

The invention further provides methods of detecting an immune response against RSV in a subject. The methods comprise contacting a biological sample from the subject with an RSV oligopeptide selected from SEQ ID NO: 3-33 and detecting an immune response. The immune response can be detected by detecting binding of antibodies in the biological sample to the RSV oligopeptide or by detecting a cellular immune response.

Definitions

The terms "adjuvant" and "immune stimulant" are used interchangeably herein, and are defined as one or more substances that cause stimulation of the immune system. The stimulation will augment or modify the immune response, e.g., by intensifying or broadening the specificity of either or both the antibody and the cellular immune response to the RSV polypeptide. In this context, an adjuvant or immune stimulant is used in the immunogenic compositions of the invention to enhance an immune response to RSV proteins. In the case where the RSV polypeptide is expressed in a viral vector, the viral vector can act as the immune stimulant.

The term "expression vector" refers to a linear or circular DNA molecule that comprises a segment encoding a polypeptide of interest (e.g., an RSV protein of the invention) operably linked to additional segments that provide for its transcription. Such additional segments include promoter and terminator sequences, and may also include one or more origins of replication, one or more selectable markers, an enhancer, a polyadenylation signal, and the like. Expression vectors are generally derived from bacterial or viral DNA, and may contain elements of both.

The terms "identical" or percent "identity," in the context of two or more nucleic acids or polypeptide sequences, (e.g., RSV proteins/peptides of the invention and polynucleotides that encode them) refer to two or more sequences or subsequences that are the same or have a specified percentage of amino acid residues or nucleotides that are the same, when compared and aligned for maximum correspondence, as measured using one of the following sequence comparison algorithms or by visual inspection.

The phrase "substantially identical," in the context of two nucleic acids or polypeptides of the invention, refers to two or more sequences or subsequences that have at least 50%, more preferably 65%, even more preferably 70%, still more preferably 75%, even more preferably 80%, and most preferably 90-95% nucleotide or amino acid residue identity, when compared and aligned for maximum correspondence, as measured using one of the following sequence comparison algorithms or by visual inspection. Preferably, the substantial identity exists over a region of the sequences that is at least about 10 or 50 residues in length, more preferably over a region of at least about 100 residues, and most preferably the sequences are substantially identical over at least about 150 residues. In a most preferred embodiment, the sequences are substantially identical over the entire length of the coding regions.

For sequence comparison, typically one sequence acts as a reference sequence (e.g., SEQ ID NO: 2), to which test sequences are compared. When using a sequence comparison algorithm, test and reference sequences are input into a computer, subsequence coordinates are designated, if necessary, and sequence algorithm program parameters are designated. The sequence comparison algorithm then calculates the percent sequence identity for the test sequence(s) relative to the reference sequence, based on the designated program parameters.

Optimal alignment of sequences for comparison can be conducted, e.g., by the local homology algorithm of Smith & Waterman, *Adv. Appl. Math,* 2:482 (1981), by the homology alignment algorithm of Needleman & Wunsch, *J. Mol. Biol.* 48:443 (1970), by the search for similarity method of Pearson & Lipman, *Proc. Nat'l. Acad. Sci, USA* 85:2444 (1988), by computerized implementations of these algorithms (GAP, BESTFIT, FASTA, and TFASTA in the Wisconsin Genetics Software Package, Genetics Computer Group, 575 Science Dr., Madison, Wis.), or by visual inspection (see generally, *Current Protocols in Molecular Biology,* F. M. Ausubel et al., eds., Current Protocols, a joint venture between Greene Publishing Associates, Inc. and John Wiley & Sons, Inc., (1995 Supplement) (Ausubel)).

Examples of algorithms that are suitable for determining percent sequence identity and sequence similarity are the BLAST and BLAST 2.0 algorithms, which are described in Altschul et al. (1990) *J. Mol. Biol.* 215: 403-410 and Altschul et al. (1977) *Nucleic Acids Res.* 25: 3389-3402, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al, supra). These initial neighborhood word hits act as seeds for initiating searches to find longer HSPs containing them. The word hits are then extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) of 10, M=5, N=−4, and a comparison of both strands. For amino acid sequences, the BLASTP program uses as defaults a wordlength (W) of 3, an expectation (E) of 10, and the BLOSUM62 scoring matrix (see Henikoff & Henikoff, *Proc. Natl. Acad. Sci. USA* 89:10915 (1989)).

In addition to calculating percent sequence identity, the BLAST algorithm also performs a statistical analysis of the similarity between two sequences (see, e.g., Karlin & Altschul, *Proc. Nat'l. Acad. Sci. USA* 90:5873-5787 (1993)). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.1, more preferably less than about 0.01, and most preferably less than about 0.001.

A further indication that two nucleic acid sequences or polypeptides of the invention are substantially identical is that the polypeptide encoded by the first nucleic acid is immunologically cross reactive with the polypeptide encoded by the second nucleic acid, as described below. Thus, a polypeptide is typically substantially identical to a second polypeptide, for example, where the two peptides differ only by conservative substitutions. Another indication that two nucleic acid sequences are substantially identical is that the two molecules hybridize to each other under stringent conditions, as described below.

"Operably linked" indicates that two or more DNA segments are joined together such that they function in concert for their intended purposes. For example, coding sequences are operably linked to promoter in the correct reading frame such that transcription initiates in the promoter and proceeds through the coding segment(s) to the terminator.

A "polynucleotide" is a single- or double-stranded polymer of deoxyribonucleotide or ribonucleotide bases typically read from the 5' to the 3' end. Polynucleotides include RNA and DNA, and may be isolated from natural sources, synthesized in vitro, or prepared from a combination of natural and synthetic molecules. When the term is applied to double-stranded molecules it is used to denote overall length and will be understood to be equivalent to the term "base pairs".

A "polypeptide" is a polymer of amino acid residues joined by peptide bonds, whether produced naturally or synthetically. Polypeptides of less than about 75 amino acid residues are also referred to here as peptides or oligopeptides.

The term "promoter" is used herein for its art-recognized meaning to denote a portion of a gene containing DNA sequences that provide for the binding of RNA polymerase and initiation of transcription of an operably linked coding sequence. Promoter sequences are typically found in the 5' non-coding regions of genes.

BRIEF DESCRIPTION OF THE DRAWINGS

FIGS. 1A-1F show purification of recombinant G protein from *E. coli* and 293 cells. (FIG. 1A) Schematic representation of the RSV G protein. RSV G protein purified from *E. coli* (REG) inclusion bodies is lacking the cytoplasmic and transmembrane domains (CT-TM) and is not glycosylated, while the RSV G protein secreted from 293-Flp-In cells (RMG) is glycosylated. N-linked glycosylation sites, as predicted by NetNGlyc 1.0 software, are represented above the bar and predicted O-linked glycosylation sites, as predicted by NetOGlyc 4.0 software, are represented below the bar in the full length RSV G and RMG proteins. REG was purified from *E. coli* inclusion bodies as described in materials and methods. RMG was purified from the clarified supernatant of 293-Flip-In cells stably expressing the RSV G protein. Both REG (FIG. 1B) and RMG (FIG. 1C) were purified through a Ni-NTA column and the final products were detected as a single band in SDS PAGE under reducing conditions (FIG. 1D) SPR interaction profile of REG and RMG binding to the protective MAb 131-2G that targets the central conserved domain of RSV G. (FIGS. 1E and 1F) Superdex S-200 gel filtration chromatography of RSV G protein produced in bacterial system (REG) (FIG. 1E) and mammalian system (RMG) (FIG. 1F). The panels present superimposed elution profiles of purified RSV G proteins (red lines) overlaid with calibration standards (grey lines).

FIGS. 4A-4C show surface plasmon resonance analysis of post-vaccination sera to REG, RMG and different antigenic regions within RSV G. (FIGS. 4A and 4B) The same individual post-vaccination mice sera from FIGS. 3A and 3B were tested for total antibody binding to the REG protein (FIG. 4A) or RMG protein (FIG. 4B) by Surface Plasmon Resonance (SPR). (FIG. 4C) Antigenic peptides representing amino acids 66-90, 90-110, 148-178, 169-207 and 236-263 of the RSV G protein were chemically synthesized and tested for binding to serum antibodies from REG or RMG immunized mice in a real time SPR kinetics experiment. Total antibody binding is represented as SPR resonance units. Sera from REG vaccinated mice showed >10 fold higher antibody binding to either REG protein (FIG. 4A) or to the glycosylated (RMG) G protein (FIG. 4B). peptide scanning showed more diverse repertoire for the REG vaccinated animals (FIG. 4C). Statistical significance was tested with one-way ANOVA and Bonferroni multiple comparisons tests. *$p<0.0001$,  $p<0.001$, *$p<0.05$.

FIGS. 5A-5C show that immunization with REG protects against homologous and heterologous RSV challenge. Mice immunized twice with PBS, REG, RMG, or F protein were challenged intranasaly (i.n.) with $1\times10^6$ pfu of RSV-A2 (FIG. 5A) or RSV-B1 (FIG. 5B) 14 days after the second immunization. Four days post virus challenge, mice lungs were collected and homogenized as described in materials and methods, and lung viral loads were determined by plaque assay. Statistical significance was tested with one-way ANOVA and Bonferroni multiple comparisons tests, *$p<0.05$. (FIG. 5C) Relationship between the total anti-G antibody binding in post-vaccination sera (in FIG. 4A) and lung viral load at 4 days post-challenge with RSV-A2 (in FIG. 5A) was analyzed and Spearman's correlation was calculated. Total antibody binding to REG is represented in resonance units and lung viral loads are represented as pfu per gram lung weight. p-values less than 0.05 were considered significant. Most animals that were immunized with REG effectively eliminated virus from the lungs after challenge with homologous (FIG. 5A) or heterologous (FIG. 5B) viruses. Most of the RMG immunized animals did not clear virus.

(FIG. 6A) Lung histology scores represent the average of 2 slides per mouse and 3 mice per group. Neutralizing antibody titers represent 50% inhibition of plaque numbers as measured by PRNT against the respective RSV strains for the 3 mice per group. 0, no lesions; 1, minimal; 2, mild; 3, modest; 4, severe. (FIG. 6B) 400× magnification images of H-E stained sectioned lungs FIGS. 7A-7I show RMG (but not REG) immunization induces high levels of Th2 cytokines and chemokines following RSV i.n challenge. (FIGS. 7A-7H) Cytokines in lung homogenates from day 2 post challenge were measured in a Bio-Plex Pro™ Mouse Cytokine assay. Values represent the concentration in pg/mL of 3 mice per group. The box extends from the $25^{th}$ to the $75^{th}$ percentile and the error bars represent the lowest and highest values. Values below the assay's limit of detection were assigned a number according to the minimum detection limit of the cytokine. The mean for each group are represented. (FIG. 7I) Ratio of the observed concentration of Th2 vs Th1 cytokines as measured by IL4/IFN-γ. Statistical significance was analyzed using a one-way ANOVA and Bonferroni multiple comparisons tests. * $p<0.0001$,  $p<0.001$, * $p<0.05$. High Th2 chemokine levels in the lung were associated with eosinophilic infiltration and sever lung pathology after challenge with RSV.

FIG. 8 shows an alignment of the full-length G protein amino acid sequence from four different RSV strains: A2 (SEQ ID NO: 34), A-Long (SEQ ID NO: 35), B-18537 (SEQ ID NO: 36), and B1 (SEQ ID NO: 37).

DETAILED DESCRIPTION

Figure 2:
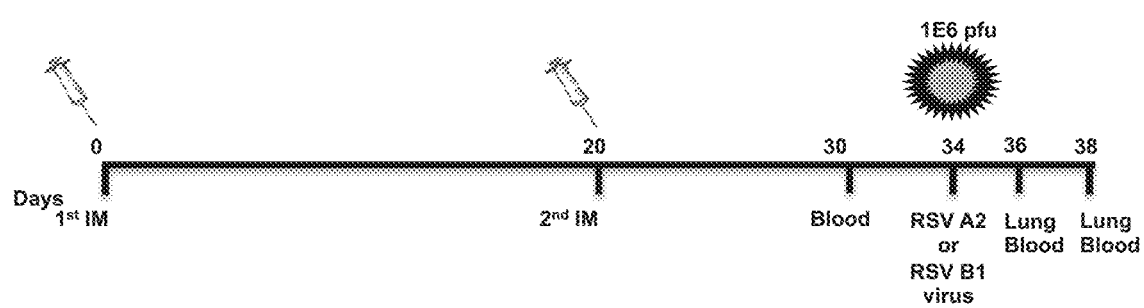
FIG. 2 is a schematic representation of mice immunization and challenge schedule. BALB/c mice were immunized i.m. with 5 µg of REG, RMG or F proteins of RSV-A2 virus strain with Emulsigen adjuvant, or with PBS control, on days 0 and 20. Ten days after the second immunization, blood was collected from the tail veins. 14 days after the second immunization, mice were challenged intranasally with $10^6$ pfu of either RSV-A2 or RSV-B1 viral strains (6-11 mice per group). Mice were sacrificed on days 2 or 4 post-challenge wherein lungs and blood were collected.

The present invention provides unglycosylated RSV polypeptides that are useful as immunogens to induce protective immune response against RSV infection. In a typical embodiment, the RSV polypeptide comprises a RSV G protein ectodomain (corresponding to amino acids 67-298 of SEQ ID NO: 34) produced as an unglycosylated protein in a prokaryotic expression system. The present invention also provides shorter RSV polypeptides (i.e., oligopeptides) that can be used in immunogenic compositions of the invention to induce protective immune responses.

RSV Polypeptides

The genome of RSV is a single, negative-sense strand of RNA of 15.2 kilobases that is transcribed by the viral polymerase into 10 mRNAs by a sequential stop-start mechanism that initiates at a single viral promoter at the 3' end of the genome. Each mRNA encodes a single major protein, with the exception of the M2 mRNA, which has two overlapping open reading frames that encode two separate proteins. The 11 RSV proteins are: the RNA-binding nucleocapsid protein (N), the phosphoprotein (P), the large polymerase protein (L), the attachment glycoprotein (G), the fusion protein (F), the small hydrophobic (SH) surface glycoprotein, the internal matrix protein (M), the two non-structural proteins NS1 and NS2, and the M2-1 and M2-2 proteins encoded by the M2 mRNA.

One of skill will recognize that any RSV protein could be used as an immunogen in the immunogenic compositions of the invention. In a typical embodiment, RSV polypeptides of the invention will be derived from either the F protein or the G protein.

The RSV G protein comprises a hydrophobic region near the N-terminus that serves as a membrane anchor, the transmembrane domain, and a C-terminal portion of the molecule exposed on the exterior side of the membrane, the ectodomain (see FIG. 1). Those of skill can readily identify the domains of a G protein using standard sequence alignments to identify corresponding residues in G proteins isolated from different RSV strains. Such an alignment is provided in FIG. 8. For example, the ectodomain of the RSV-A2 strain, which is exemplified below, extends from residues 67-298 of SEQ ID NO: 34). Using standard sequence alignment techniques, one of skill can readily determine the corresponding residues in other RSV strains. For example, to determine which amino acid of a first protein "corresponds" to the position of an amino acid in a second protein, the amino acid sequences of the two proteins are optimally aligned (e.g., using a BLAST algorithm).

The RSV polypeptides of the invention are typically fragments of a native RSV protein, such as an F protein or a G protein. In a typical embodiment, the RSV polypeptide is from about 10 amino acids to about 75 amino acids in length (also be referred to as RSV oligopeptides). The RSV oligopeptides may also be less than about 50 amino acids in length. Exemplary RSV oligopeptides of the invention are provided in SEQ ID NOs: 3-33. Peptides of particular interest include the following peptides.

RSV-F Peptide Sequences:

```
101-157
                                    (SEQ ID NO: 5)
PATNNRARRELPRFMNYTLNNAKKTNVTLSKKRKRRFLGFLLGVG

SMASGVAVSKV 195-240
                                    (SEQ ID NO: 12)
LKNYIDKQLLPIVNKQSCSISNIETVIEFQQKNNRLLEITREFSVN 425-450
                                    (SEQ ID NO: 19)
SNKNRGIIKTFSNGCDYNTSNKGVDTV 443-461
                                    (SEQ ID NO: 20)
SNKGVDTVSVGNTLYYVNK
```

RSV-G Peptide Sequences:

```
    129-152
                                    (SEQ ID NO: 28)
    TTVKTKNTTITTQTQPSKPTTKQRQ 169-207
                                    (SEQ ID NO: 30)
    NFVPCSICSNNPTCWAICKRIPNKKPGKKTTTKPTKKPT 263-298
                                    (SEQ ID NO: 33)
    ETFHSTSSEGNPSPSQVSTTSEYPSQPSSPPNTPRQ
```

The RSV polypeptides of the invention may be multimeric and comprise more than one of the RSV oligopeptides of the invention in a single polypeptide chain. Such multimeric polypeptides may, for example, comprise multiple copies of a single oligopeptide or may comprise different oligopeptide sequences. The multimeric RSV polypeptides may also comprise oligopeptide sequences from other pathogens so that immune protection against multiple pathogens is provided in a single composition. The multimeric RSV polypeptides will typically be from about 50 to about 300 amino acids in length.

In other embodiments, the RSV polypeptides of the invention are about 75 to about 250 amino acids in length and are derived from the ectodomain of an RSV G or F protein. More typically, the RSV polypeptide is from about 150 to about 230 amino acids in length. In these embodiments, the RSV polypeptide will consist essentially of the ectodomain of a G protein (e.g., those residues corresponding to residues 67-298 of the RSV-A2 strain G protein, SEQ ID NO: 34 or 67-299 of the RSV-B1 strain G protein, SEQ ID NO: 37). Alternatively, the RSV polypeptide of the invention may consist essentially of the ectodomain of an F protein (e.g., those residues corresponding to residues 23-524 of the RSV-A2 strain F protein, SEQ ID NO: 39). In such an embodiment, the RSV polypeptide consisting essentially of the ectodomain of a G or F protein may comprise, for example, an epitope tag or other short sequence to facilitate purification of the polypeptide (e.g., a polyhistidine tag). An RSV polypeptide consisting essentially of the ectodomain of a G or F protein may also comprise less than about 10 amino acids, usually less than about 5 amino acids, from the G or F protein transmembrane domain.

The RSV polypeptide is typically unglycosylated. An "unglycosylated RSV polypeptide" is one that lacks at least about 95% of the sugar moieties that occur on the naturally occurring RSV protein. Usually, the unglycosylated RSV polypeptide lacks at least about 99% of the sugar moieties. In the most embodiments, the RSV polypeptide is completely unglycosylated. In a typical embodiment, the unglycosylated RSV polypeptide is expressed in a prokaryotic organism (e.g. *E. coli*) that does not comprise the cellular machinery to glycosylate proteins. The unglycosylated RSV polypeptide may also be chemically synthesized or expressed in a glycosylation-deficient mammalian cell. Alternatively, appropriate enzymes may be used in vitro to remove all or most of the sugar moieties from the polypeptide.

The RSV polypeptides of the invention can be used in immunogenic compositions, as well a variety of other uses. For example, the polypeptides can be used in serological assays for diagnosis of RSV, in analysis of immune sera from pre-clinical and clinical trials of RSV vaccines, and in mapping of monoclonal and polyclonal antibodies against different RSV proteins. The oligopeptides are also useful in studies designed to understand viral pathogenesis and therefore useful in designing antiviral drugs or treatment. For example, the peptides can be used to study viral protein-protein, viral RNA-protein and viral-host protein interactions.

The RSV polypeptides of the invention can be made using standard methods well known to those of skill in the art. For example, shorter polypeptides (i.e., oligopeptides) can be made synthetically. For longer polypeptides, recombinant expression can be conveniently used. Recombinant expression in a variety of host cells, including *E. coli*, or other prokaryotic hosts which lack the cellular machinery for glycosylation of proteins is well known in the art.

Polynucleotides encoding RSV polypeptides, recombinant expression vectors, and host cells containing the recombinant expression vectors, as well as methods of making such vectors and host cells by recombinant methods are useful to produce the polypeptides of the invention. These methods are well are well known to those of skill in the art.

The polynucleotides encoding RSV polypeptides may be synthesized or prepared by techniques well known in the art. Nucleotide sequences encoding the RSV polypeptides of the disclosure may be synthesized, and/or cloned, and expressed according to techniques well known to those of ordinary skill in the art. In some embodiments, the polynucleotide sequences will be codon optimized for a particular recipient using standard methodologies. For example, a DNA construct encoding a RSV polypeptide can be codon optimized for expression in prokaryotic hosts, e.g., bacteria.

Examples of useful bacteria include, but are not limited to, *Escherichia, Enterobacter, Azotobacter, Erwinia, Bacillus, Pseudomonas, Klebsiella, Proteus, Salmonella, Serratia, Shigella, Rhizobia, Vitreoscilla,* and *Paracoccus.* The nucleic acid encoding the RSV polypeptide is operably linked to appropriate expression control sequences for each host. For *E. coli* this includes a promoter such as the T7, trp, or lambda promoters, a ribosome binding site and preferably a transcription termination signal. For eukaryotic cells, the control sequences will include a promoter and preferably an enhancer derived from immunoglobulin genes, SV40, cytomegalovirus, etc., and a polyadenylation sequence, and may include splice donor and acceptor sequences.

The RSV polypeptides may also be expressed in other cells that normally glycosylate proteins, such as mammalian, insect, plants or yeast cells. In some embodiments, the polypeptide is deglycosylated after expression. Removal of carbohydrate moieties may be accomplished chemically or enzymatically according to well-known techniques. Chemical deglycosylation typically involves contacting the polypeptide with trifluoromethanesulfonic acid, or an equivalent compound. This treatment results in the cleavage of most or all sugars except the linking sugar (N-acetylglucosamine or N-acetylgalactosamine), while leaving the polypeptide intact. Enzymatic cleavage of carbohydrate moieties on proteins can be achieved by the use of a variety of endo- and exo-glycosidases. Kits for enzymatic removal of carbohydrates are commercially available.

Once expressed, the recombinant RSV polypeptides can be purified according to standard procedures of the art, including ammonium sulfate precipitation, affinity columns, column chromatography, gel electrophoresis and the like. In a typical embodiment, the recombinantly produced RSV polypeptide is expressed as a fusion protein that has a "tag" at one end which facilitates purification of the polypeptide. Suitable tags include epitope tags, which are amino acid sequences that are specifically recognized by an antibody. Epitope tags are generally incorporated into recombinantly expressed proteins to enable the use of a readily available antibody to detect or isolate the protein. Other suitable tags are known to those of skill in the art, and include, for example, an affinity tag such as a polyhistidine tag which will bind to metal ions such as nickel or cobalt ions.

Immunogenic Compositions

The RSV polypeptides and oligopeptides of the invention may be formulated as a vaccine (also referred to as an "immunogenic composition") according to methods well known in the art. Such compositions will typically include immune stimulants to enhance immune responses. The optimal ratios of each component in the formulation may be determined by techniques well known to those skilled in the art. The immunogenic compositions may be administered to a patient or subject according to standard techniques well-known to those of skill in the art. The subject will typically be a human, or non-human animal (e.g., cattle, horses, pigs, dogs, and cats). The human patient or subject may be an adult and child. In a typical case the subject will be an infant (e.g., a newborn), a young child, a pregnant mother, a woman of child bearing age, or the elderly.

The immunogenic compositions may also comprise one or more of the RSV oligopeptides shown in SEQ ID NOs: 3-33 or a multimeric RSV polypeptide comprising one of more the oligopeptide sequences. The oligopeptides or multimeric polypeptide may be unglycosylated or glycosylated. For example, the composition may comprise only one of the following oligopeptides: SEQ ID NO: 3, SEQ ID NO: 4, SEQ ID NO: 5, SEQ ID NO: 6, SEQ ID NO: 7, SEQ ID NO: 8, SEQ ID NO: 9, SEQ ID NO: 10, SEQ ID NO: 11, SEQ ID NO: 12, SEQ ID NO: 13, SEQ ID NO: 14, SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, SEQ ID NO: 29, SEQ ID NO: 30, SEQ ID NO: 31, SEQ ID NO: 32, or SEQ ID NO: 33. In some embodiments, the composition will further comprise additional oligopeptides selected from the same list of peptides. Alternatively, the oligopeptides may be included in a single, multimeric RSV polypeptide.

The preparation and use of immunogenic compositions are well known to those of skill in the art. Liquid pharmaceutical compositions generally include a liquid carrier such as water, petroleum, animal or vegetable oils, mineral oil or synthetic oil. Physiological saline solution, dextrose or other saccharide solution or glycols such as ethylene glycol, propylene glycol or polyethylene glycol may be included.

Polynucleotides encoding the RSV polypeptides of the invention can also be administered to the subject. Typically, an expression cassette suitable for driving expression in human cells is prepared. This approach is described, for instance, in Wolff (1990) Science 247:1465-1468; U.S. Pat. Nos. 5,580,859 and 5,589,466.

The RSV polypeptides (e.g., multimeric RSV polypeptides) may also be expressed in replication deficient or competent viral vectors that comprise nucleic acids encoding them. Such viral vectors include, for example, adenoviral vectors, vaccinia virus vectors, avipox vector such as fowlpox or canarypox, herpes virus vectors, a vesicular stomatitis virus vectors, or alphavirus vectors. One of skill will recognize that the immunogenic compositions of the invention may comprise multiple antigens and vectors. In such embodiments, the viral vector can act as an immune stimulant. Thus, the immune stimulant of the immunogenic compositions of the invention will be the vector itself and addition of further immune stimulants may not be necessary.

The RSV polypeptides (e.g., multimeric RSV polypeptides and RSV oligopeptides) may also be administered in combination with nanoparticles (i.e., particulate material with size 1-1000 nm). A great variety of materials can be used to prepare nanoparticles useful in the immunogenic compositions of the invention. For example, synthetic polymers such as poly(d,l-lactide-co-glycolide) (PLG), poly(d,l-lactic-coglycolic acid)(PLGA), poly(g-glutamic acid) (g-PGA), polyethylene glycol) (PEG) and polystyrene can be conveniently used. Polymeric nanoparticles entrap the RSV polypeptides for delivery to certain cells or sustain antigen release as a result of their slow biodegradation rate. Natural polymers based on polysaccharide may also be used. Examples include pullulan, alginate, inulin and chitosan. Inorganic nanoparticles useful in the invention include gold nanoparticles, which can be surface-modified with carbohydrates, carbon nanoparticles or silica-based nanoparticles.

The compositions are suitable for single administrations or a series of administrations. When given as a series, inoculations subsequent to the initial administration are given to boost the immune response and are typically referred to as booster inoculations. The compositions of the invention can be used as a boosting composition primed by antigen using any of a variety of different priming compositions, or as the priming composition. Thus, one aspect of the present invention provides a method of inducing and/or boosting an immune response to an antigen in an individual.

The timing of the administration of boosting compositions is well within the skill in the art. Boosting composition are generally administered weeks or months after administration of the priming composition, for example, about 2-3 weeks or 4 weeks, or 8 weeks, or 16 weeks, or 20 weeks, or 24 weeks, or 28 weeks, or 32 weeks.

The compositions of the invention may comprise other RSV immunogens or the priming or boosting inoculations may comprise other immunogens. The other immunogens used in combination with the RSV polypeptides of the invention are not critical to the invention. Examples of such immunogens include those from Influenza, Hepatitis and other childhood infectious diseases.

The immunogens in the respective priming and boosting compositions (however many boosting compositions are employed) need not be identical, but should share epitopes. The immunogen may correspond to a complete antigen in a target pathogen or cell, or a fragment thereof. Peptide epitopes or artificial strings of epitopes may be employed, more efficiently cutting out unnecessary protein sequence in the antigen and encoding sequence in the vector or vectors. For example, one or more additional epitopes may be included, for instance epitopes which are recognized by T helper cells, especially epitopes recognized in individuals of different HLA types.

As noted above, the immunogenic compositions of the invention may comprise an immune stimulant (also referred to as an adjuvant). In those embodiments in which the RSV polypeptide is expressed in a viral vector, the immune stimulant is typically the viral vector, itself. Adjuvants suitable for co-administration in accordance with the present invention should be ones that are potentially safe, well tolerated and effective in people including QS-21, Detox-PC, MPL-SE, MoGM-CSF, TiterMax-G, CRL-1005, GERBU, TERamide, PSC97B, Adjumer, PG-026, GSK-I, GcMAF, B-alethine, MPC-026, Adjuvax, CpG ODN, Betafectin, Alum, and MF59.

Other immune stimulants that may be administered include lectins, growth factors, cytokines and lymphokines such as alpha-interferon, gamma interferon, platelet derived growth factor (PDGF), granulocyte-colony stimulating factor (GCSF), granulocyte macrophage colony stimulating factor (GMCSF), tumor necrosis factor (TNF), epidermal growth factor (EGF), IL-1, IL-2, IL-4, IL-6, IL-8, IL-10, and IL-12 or encoding nucleic acids therefore.

As noted above, the compositions of the invention may comprise a pharmaceutically acceptable excipient, carrier, buffer, stabilizer or other materials including particles (e.g., nanoparticles) well known to those skilled in the art. Such materials should be non-toxic and should not interfere with the efficacy of the active ingredient. The precise nature of the carrier or other material may depend on the route of administration, e.g., oral, intravenous, cutaneous or subcutaneous, intramucosal (e.g., gut), intranasal, intramuscular, or intraperitoneal routes. Administration is typically intradermal, e.g., subcutaneous or intramuscular.

Intramuscular administration of the immunogenic compositions may be achieved by using a needle to inject a suspension of the RSV polypeptide or nucleic acid encoding it. An alternative is the use of a needleless injection device to administer the composition (using, e.g., Biojector™) or a freeze-dried powder containing the vaccine.

For intravenous, cutaneous or subcutaneous injection, or injection at the site of affliction, the RSV polypeptide will be in the form of a parenterally acceptable aqueous solution which is pyrogen-free and has suitable pH, isotonicity and stability. Those of skill in the art are well able to prepare suitable solutions using, for example, isotonic vehicles such as Sodium Chloride Injection, Ringer's Injection, Lactated Ringer's Injection, Preservatives, stabilizers, buffers, antioxidants and/or other additives may be included, as required. A slow-release formulation may also be employed.

Typically, administration will have a prophylactic aim to generate an immune response against a RSV antigen before infection or development of symptoms. Diseases and disorders that may be treated or prevented in accordance with the present invention include those in which an immune response may play a protective or therapeutic role. In other embodiments, the RSV polypeptides can be administered for post-exposure prophylactics.

The immunogenic compositions containing the RSV polypeptide or polynucleotides encoding them are administered to a subject, giving rise to an anti-RSV immune response in the subject. An amount of a composition sufficient to in induce a detectable immune response is defined to be an "immunologically effective dose." As shown below, the immunogenic compositions of the invention induce an antibody response, as well as a CD8+ cell immune response. In a typical embodiment the immune response is a protective immune response.

The actual amount administered, and rate and time-course of administration, will depend on the nature and severity of what is being treated. Prescription of treatment, e.g., decisions on dosage etc., is within the responsibility of general practitioners and other medical doctors, or in a veterinary context a veterinarian, and typically takes account of the disorder to be treated, the condition of the individual patient, the site of delivery, the method of administration and other factors known to practitioners. Examples of the techniques and protocols mentioned above can be found in Remington's Pharmaceutical Sciences, 16th edition, Osol, A. ed., 1980.

In one exemplary regimen, the RSV polypeptide is administered (e.g., intramuscularly) at a dose of 10 micrograms to 1 milligram/injection. A boost can be administered up to 4 weeks later. The composition may, if desired, be presented in a kit, pack or dispenser, which may contain one or more unit dosage forms containing the active ingredient. The kit, for example, may comprise metal or plastic foil, such as a blister pack. The kit, pack, or dispenser may be accompanied by instructions for administration.

The compositions of the invention may be administered alone or in combination with other treatments, either simultaneously or sequentially dependent upon the condition to be treated.

Detection of Immunoresponses

The RSV polypeptides (particularly oligopeptides) of the invention are useful in the detection of RSV infection. Methods for detecting humoral or cellular immune responses in biological samples are well known in the art. As used herein, a "biological sample" is any lymphocyte or antibody-containing sample obtained from a patient. For example, the sample can be whole blood, sputum, serum, plasma, saliva cerebrospinal fluid or urine. The polypeptides of the invention are used in an assay, for example as described below, to determine the presence or absence of antibodies or immune cells (e.g., lymphocytes, CD4+ T-cells, CD8+ T-cells, B-cells, NK cells, mast cells, antigen presenting cells) or cytokines induced by RSV antigens. The presence of such antibodies or immune cells indicates previous sensitization to RSV antigens which may be indicative of RSV infection.

There are a variety of assay formats known to those of ordinary skill in the art for using one or more oligopeptides to detect antibodies in a sample. For example, the assay may involve the use of an RSV polypeptide immobilized on a solid support to bind to and remove the antibodies from the sample. The assay may also involve the capture of the RSV polypeptide by an antibody or binding protein (e.g., protein A, protein G, protein A/G, avidin, streptavidin, etc.) bound to a solid support. The assay may involve the labeling of the RSV polypeptide with small molecules such as biotin, enzymes, or fluorophores. Alternatively, antibodies from patients could be bound to a solid phase using binding proteins or type specific antibodies (e.g., anti-human IgM or IgG antibodies), followed by treatment with the labeled or unlabeled RSV polypeptides, and finally detecting the bound RSV polypeptide with a conjugated antibody and/or a binding protein (e.g., avidin-FITC, avidin-peroxidase, etc.). The bound antibody may then be detected using a detection reagent that contains a reporter group. Suitable detection reagents include antibodies that bind to the solid phase bound RSV polypeptide or antibody/polypeptide complex or to free polypeptide labeled with a reporter group (e.g., in a semi-competitive assay). Alternatively, a competitive assay may be utilized, in which an antibody that binds to the polypeptide is labeled with a reporter group and allowed to bind to the immobilized antigen after incubation of the antigen with the sample. The extent to which components of the sample inhibit the binding of the labeled antibody to the polypeptide is indicative of the reactivity of the sample with the immobilized polypeptide. In certain embodiments, the assay is an enzyme linked immunosorbent assay (ELISA), chemiluminescent assay, or fluorescence assay.

Methods for detecting cellular immune responses are also well known. In such assays antigen presenting cells, immune cells (e.g., CD8+ T-cells, CD4+ T-cells, B-cells, etc.) and RSV polypeptides of the invention are incubated under appropriate conditions to induce proliferation or activation of immune effector cells (e.g., CD8+ CD4+ T-cells, B-cells, NK and iNKT cells, etc.) specific to RSV. The antigen-specific responses of induced immune effector cells (e.g., helper T-cells, CTLs, B-cells, NK, NKT, etc.) can be detected by a number of techniques (e.g., by a $^{51}$Cr release assay, $^{3}$H-thymidine incorporation, CFSE and other FACS-analysis proliferation assays, cytokine intracellular staining and FACS analysis, ELISPOT, detection of secreted cytokines such as INF-γ).

EXAMPLES

The following examples are offered to illustrate, but not to limit the claimed invention.

Example 1

We have performed a large scale analysis of epitopes recognized by post-RSV vaccination sera that identified multiple protective vaccine targets against RSV. These peptide epitopes were chemically synthesized, tested for antibody binding. This was carried out using a "Whole Genome Phage Display Library" (GFPDL) expressing all the possible peptides from the RSV G and F protein and screening with polyclonal immune sera from immunized rabbits immunized with unglycosylated F and G proteins of RSV. Each phage in the library expresses on its surface a fragment of the RSV membrane proteins in fusion with the phage gIII protein. The antibody bound phages were amplified and the inserts are sequenced. Unlike the native RSV G and F proteins, which is heavily glycosylated, the phage library expresses only unglycosylated peptides. The peptides identified in the screen were then used to immunize rabbits using standard techniques. Following immunization these animal sera were tested in multiple RSV neutralization assays. The results, shown in Table 1, show that most of these peptides generated neutralizing antibodies against RSV. Those peptides that generated neutralizing antibodies are shown in SEQ ID NOs: 3-33. These peptides can be an important target for development of peptide based RSV diagnosis, treatment and vaccines against RSV infection and disease.

Material and Methods

Cell, Viruses and Plasmids

Vero cells (CCL-81) and A549 cells (CCL-185) were obtained from the ATCC 293-Flp-In cells (R750-07) were obtained from Invitrogen. Vero cells, A549 cells and 293-Flp-In cells were grown in EMEM medium, F12K medium and D-MEM (high glucose) respectively. All cell lines were supplemented with 10% heat inactivated fetal bovine serum (FBS) and 1× Penicillin/Streptomycin (P/S) and L-glutamine and maintained in an incubator at 37° C. and 5% $CO_2$.

RSV virus, strains A2 (NR-12149) and B1 (NR-4052) were obtained from BEI Resources, NIAID, NIH. All virus stocks were prepared by infecting a sub-confluent A549 cell monolayers with virus in F12K media with L-glutamine supplemented with 2% FBS and 1× P/S (infection media). Virus was collected 3-5 days post-infection (dpi) by freeze-thawing cells twice and combining with supernatant. Virus harvests were cleared of cell debris by centrifugation at 3,000 rpm for 15 min. Virus stocks to be used in challenged

TABLE 1

| F-peptides | | Rabbit Sera Neutralization |
|---|---|---|
| A.A. | Sequence | titers |
| 1-34 | MELLILKANAITTILTAVTFCFASGQNITEEFYQ (SEQ ID NO: 3) | 24 |
| 101-121 | PATNNRARRELPRFMNYTLNN (SEQ ID NO: 7) | 13 |
| 174-203 | TNKAVVSLSNGVSVLTSKNVLDLKNYIDKQL (SEQ ID NO: 9) | 13 |
| 195-240 | LKNYIDKQLLPIVNKQSCSISNIETVIEFQQKNNRLLEITREFSVN (SEQ ID NO: 12) | 17 |
| 234-287 | TREFSVNAGVTTPVSTYMLTNSELLSLINDMPITNDQKKLMSNNVQIVRQQSYS (SEQ ID NO: 14) | 14 |
| 250-273 | YMLTNSELLSLINDMPITNDQKKL (SEQ ID NO: 15) | 12 |
| 425-450 | SNKNRGIIKTFSNGCDYVSNKGVDTV (SEQ ID NO: 19) | 59 |
| 443-461 | SNKGVDTVSVGNTLYYVNK (SEQ ID NO: 20) | 96 |
| 471-493 | GEPIINFYDPLVFPSDEFDASIS (SEQ ID NO: 22) | 18 |
| 552-572 | ARSTPVTLSKDQLSGINNIAF (SEQ ID NO: 24) | 13 |
| G-peptides | | |
| A.A. | Sequence | |
| 33-61 | LNLKSVAQITLSILAMIISTSLIIAAIIF (SEQ ID NO: 25) | |
| 66-90 | NHKVTPTTAIIQDATSQIKNTTPTY (SEQ ID NO: 26) | 24 |
| 90-110 | YLTQNPQLGISPSNPSEITSQ (SEQ ID NO: 27) | 16 |
| 129-152 | TTVKTKNTTTTQTQPSKPTTKQRQ (SEQ ID NO: 28) | 28 |
| 148-178 | TTKQRQNKPPSKPNNDFHFEVFNFVPCSICS (SEQ ID NO: 29) | 47 |
| 169-207 | NFVPCSICSNNPTCWAICKRIPNKKPGKKTTTKPTKKPT (SEQ ID NO: 30) | 683 |
| 236-263 | INTTKTNIITTLLTSNTTGNPELTSQME (SEQ ID NO: 31) | 19 |

Example 2

New efforts are under way to develop vaccines against RSV that will provide protective immunity without the potential for disease enhancement. The G attachment protein represents an important candidate for inclusion in an effective RSV vaccine. In the current study, we evaluated the safety and protective efficacy of RSV A2 recombinant unglycosylated. G protein ectodomain produced in *E. coli* (REG) vs. glycosylated. G produced in mammalian cells (RMG) in a mouse RSV challenge model (A2 and B1 strains). The unglycosylated G generated high protective immunity and no lung pathology even in animals that lacked anti-RSV neutralizing antibodies prior to RSV challenge. Control of viral loads correlated with antibody binding to the G protein. In contrast, the glycosylated G protein provided poor protection and enhanced lung pathology after RSV challenge. Therefore, bacterially produced unglycosylated G protein presents an economical approach for protective vaccine against RSV.

studies were pelleted by centrifugation at 7,000 rpm overnight. Pelleted virus was resuspended in F12K media supplemented with 50 mM HEPES and 100 mM $MgSO_4$, aliquoted and frozen at −80° C. until needed. Virus titers were determined by plaque assay in Vero cells.

Codon optimized RSV-G coding DNA for *E. coli* and mammalian cells were chemically synthesized. A NotI and PacI site was used for cloning the RSV A2 G ectodomain coding sequence (67-298) in the T7 based pSK expression vector (19) for bacterial expression and the pSecR vector for mammalian expression (20) to express G protein in *E. coli* and in 293Flp-In cells, respectively.

Purified RSV A2 F protein encoding amino acids 22-529 and fused to a polyhistidine tag produced in insect cells with endotoxin levels <1 EU/μg of protein was obtained from Sino biologicals.

Production of Recombinant G Protein from *E. coli* (REG)

Recombinant RSV G 67-298 extracellular domain was expressed in *E. coli* BL21(DE3) cells (Novagen) and was purified as described previously (19, 21). Briefly, G protein expressed and localized in *E. coli* inclusion bodies (IB) was isolated by cell lysis and multiple washing steps with 1% Triton X-100. The pelleted IB containing G protein was resuspended in denaturation buffer and centrifuged to remove debris. The protein supernatant was renatured by slowly diluting the redox folding buffer. The renatured protein solution was dialyzed against 20 mM Tris-HCl pH 8.0 to remove the denaturing agents. The dialysate was filtered through a 0.45 μm filter and was purified through a HisTrap FF chromatography column (GE Healthcare). Protein concentration was analyzed by BCA (Pierce) and purity of the purified REG protein was determined by SDS-PAGE. Endotoxin levels of the purified protein were <1 EU/μg of protein.

Production of Recombinant Glycosylated G Protein Using 293 Flp-In Cells (RMG)

293-Flp-In cells and pOG44 (plasmid expressing Flp-In recombinase) were obtained from Invitrogen (Carlsbad, Calif.). The 293-Flp-In cell line stably expressing the RSV A2 G protein was developed as described previously (20). Briefly, 293-Flp-In cells were transfected with the plasmids expressing Flp-In recombinase and the RSV A2 G ectodomain in DMEM media (Invitrogen). Twenty four hours after transfection, culture medium was replaced with fresh DMEM containing 150 μg/mL of hygromycin for selection of stably transfected cells. For protein expression, cells were maintained in 293-Expression media (Invitrogen), and cell supernatant was collected every 3-4 days. Supernatant was cleared by centrifugation and filtered through a 0.45 μm filter before purification through a His-Trap FF column (GE healthcare)

Gel Filtration Chromatography

Proteins at a concentration of 5 mg/ml were analyzed on Superdex S200 XK 16/60 column (GE-Healthcare) pre-equilibrated with PBS, and the protein elution was monitored at 280 nm. Protein molecular weight marker standards (GE healthcare) were used for column calibration and generation of standard curves to identify the molecular weights of the test protein samples.

Plaque Reduction Neutralization Test (PRNT)

For PRNT, heat-inactivated sera was diluted 4-fold and incubated with 20-60 pfu of RSV from strain A2 or B1 for 1 hr at 37° C. and 5% $CO_2$ and the assay was performed in presence of 5% Guinea Pig complement as described previously (22). Briefly, Vero cells were infected with sera:virus mix and incubated for 1 hr before removing the inoculum and adding an overlay of 0.8% methylcellulose in infection media. Plates were incubated for 5-7 days and plaques were detected by immunostaining. Neutralization titers were calculated by adding a trend-line to the neutralization curves and using the following formula to calculate 50% end-point titers: antilog of [(50+y-intercept)/slope].

Mice Immunization, RSV Challenge and Sample Collection

All animal experiments were approved under animal protocol study number #2009-20 by the US FDA Institutional animal care and use committee. Four to six week old female BALB/c mice were obtained from NCI (Frederick, Md.). Mice were immunized intramuscularly at day 0 and day 20 with 5 μg of purified RSV protein combined with Emulsigen adjuvant. Blood was collected by tail vein on days 0, 14 and 30. On day 34, mice were anesthetized with ketamine/xylazine cocktail and infected intranasally (i.n.) with $10^6$ pfu of RSV from strain A2 or B1. Mice were sacrificed by $CO_2$ asphyxiation either two or four days post-RSV challenge, wherein blood and lungs were collected. For histopathology analysis of lungs, the right lobe of the lung was collected on days 2 and 4 post RSV challenge by inflation with 10% neutral buffered formalin. For viral load determination and cytokine analysis the left lobe of the lung was collected.

Lung Viral Load Determination

Lungs were weighed and homogenized in F12K/2% FBS/1× P/S (5 mL media/gram of lung) using Omni tissue homogenizer (Kennesaw, Ga.). The supernatant was cleared by centrifugation at 3,000 rpm for 10 min and used immediately for viral titration with a plaque assay as described above in Vero cells.

Measurement of Cytokine Levels in the Lung

All lungs were weighed and homogenized in 5 mL media/gram of lung, as described above, to normalize amount of lung tissue used per sample. Homogenized lungs were further diluted in infection culture media containing 2× concentration of Complete-EDTA Free protease inhibitor cocktail (Roche, Basel, Switzerland) and used in a Bio-Flex Pro™ Mouse Cytokine 23-plex assay following the manufacturers recommendations. Plates were read using a Bio-Plex 200 System (Biorad, Hercules, Calif.).

Lung Histopathology

Lungs were fixed in situ with 10% neutral buffered formalin and removed from chest cavity. Fixed lungs were embedded into a paraffin block, sectioned and stained with hematoxylin and eosin (H&E) by Histoserv. Three mice per immunization and two slides per mouse were analyzed for histopathology. The slides were reviewed with an Olympus BX41 microscope. Photomicrographs were taken with the microscope, an Olympus DP71 digital camera and images captured using Olympus cellSens software. Lung lesions in each mouse were graded (scored) according to the severity of each category for following criteria: whole lung section, bronchiolar lesions, vascular lesion and alveolar lesions. Severity score was 0, no lesions; 1, minimal lesions; 2, mild lesions; 3, moderate lesions; 4, severe lesions.

Surface Plasmon Resonance (SPR)

Steady-state equilibrium binding of post-vaccinated mouse sera was monitored at 25° C. using a ProteOn surface plasmon resonance biosensor (BioRad). The recombinant G proteins from *E. coli* (REG) or 293T cells (RMG) were coupled to a GLC sensor chip with amine coupling with 500 resonance units (RU) in the test flow channels. Samples of 100 μl freshly prepared sera at 10-fold dilution or Mabs (starting at 1 μg/ml) were injected at a flow rate of 50 μl/min (120 sec contact time) for association, and disassociation was performed over a 600 second interval: Responses from the protein surface were corrected for the response from a mock surface and for responses from a buffer only injection. Pre-vaccination mouse sera were used as a negative control. Total antibody binding and data analysis results were calculated with BioRad ProteOn manager software (version 2.0.1).

Statistical Analyses

The statistical significances of group differences were determined using a one-way ANOVA and Bonferroni multiple comparisons test. Correlations were calculated with a Spearman's two-tailed test. p-values less than 0.05 were considered significant with a 95% confidence interval.

Results

Expression and Purification of Glycosylated and Non-Glycosylated RSV G Protein

The RSV G protein from the A2 strain is a heavily glycosylated protein of 298 amino acids with several N-linked and O-linked glycosylation sites in its native form (FIG. 1A) (23). To determine the impact of glycosylation on G protein immunogenicity, a non-glycosylated extracellular domain of G protein from RSV-A2 strain was recombinantly produced in *E. coli* and termed REG (FIG. 1A). Insoluble G protein was purified from *E. coli* inclusion bodies, denatured, renatured under controlled redox refolding conditions and purified by Ni-NTA chromatography as described in materials and methods. Purified REG protein displayed a single ~36 kDa molecular weight protein under reducing conditions in SDS-PAGE (FIG. 1B) that was recognized by rabbit anti-G antibodies when tested in western blot assay (data not shown). To produce a native glycosylated extracellular G protein (FIG. 1A), 293-Flp-In cells were stably transfected with plasmid expressing the ectodomain of the RSV A2 G coding sequence and secreted glycosylated G-protein in the mammalian cell culture supernatant was purified by Ni-NTA chromatography and termed RMG. Purified glycosylated G protein (RMG) exists as a single band of ~90 kDa under reducing conditions (FIG. 1C) similar to native viral G protein that was recognized by rabbit anti-G polyclonal sera in a western blot (data not shown). In addition, both G ectodomains were recognized equally by G-specific MAb 131-2G, which binds to the central conserved region of the RSV G protein (24, 25) (FIG. 1D)

To determine if these purified recombinant proteins contain higher order quaternary forms, the purified RSV G proteins were subjected to size exclusion gel filtration chromatography (FIGS. 1E and F). The in-vitro refolded bacterially produced recombinant RSV G (REG) extracellular domain (67-298) contained three molecular weight (MW) forms representing approximately equal amounts of monomers, tetramers and higher order oligomeric form (FIG. 1E). In comparison, the glycosylated RSV G (RMG) extracellular domain (67-298) purified from proteins secreted in supernatant from 93-Flp-In mammalian cell culture contained only oligomeric form (FIG. 1F).

Figure 3A:
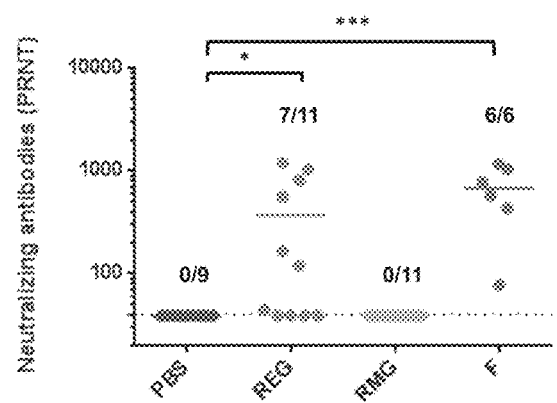
FIGS. 3A and 3B show a neutralizing antibody response following RSV G (REG, RMG) and F protein immunization. Serum from individual mice collected on day 10 post second immunization was tested for neutralization in a plaque reduction neutralization test (PRNT) against the homologous RSV-A2 strain (FIG. 3A) or heterologous RSV-B1 strain (FIG. 3B). Neutralizing antibody titers represent 50% inhibition of plaque numbers. The average for each group is represented with a horizontal line. Pre-vaccination (day 0) serum samples from all the animals tested negative in PRNT (data not shown). 7/11 animals vaccinated with unglycosylated G ectodomain (REG) generated good neutralization titers against the RSV A2 strain. No animals vaccinated with the glycosylated G ectodomain (RMG) generated neutralizing antibodies against RSV A2. Statistical significance was tested with one-way ANOVA and Bonferroni multiple comparisons tests. * $p<0.0001$,  $p<0.001$, *$p<0.05$.
Figure 3B:
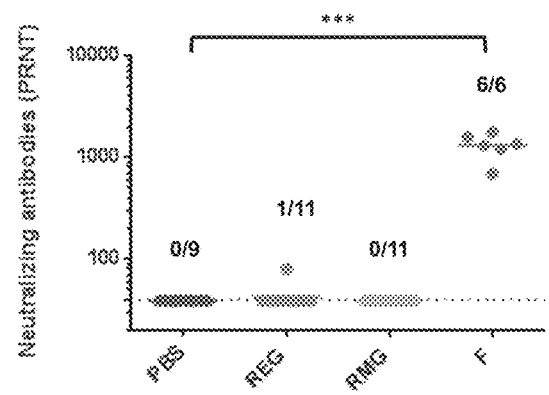

Immunization of Mice with Non-Glycosylated REG Protein Generates Higher Binding and Neutralizing Antibody Titers Compared with Glycosylated RMG Protein The RSV G protein is one of the most immunogenic proteins of RSV (26, 27). To test the antigenicity of glycosylated (RMG) versus non-glycosylated (REG) G protein, BALB/c mice were immunized twice, 20 days apart, with 5 µg of REG, RMG, or F protein from RSV A2 strain adjuvanted with Emulsigen, or were mock vaccinated with PBS (FIG. 2). To test if immunization with REG or RMG protects mice from RSV challenge, 14 days after the second immunization all animals were challenged with either RSV A2 (vaccine strain) or with the heterologous RSV B1 strain. Sera collected after the second immunization were tested for RSV-neutralizing activity in plaque reduction neutralization test (PRNT). Pre-vaccination (day 0) serum samples from all the animals tested negative in PRNT (data not shown). As expected, mice immunized with the F protein had high levels of neutralizing antibodies against both RSV strains, while mice immunized with PBS did not have detectable levels of anti-RSV neutralizing antibodies (FIG. 3A-B). In mice immunized with REG, 7 out 11 (67%) had neutralizing antibodies against homologous RSV-A2 virus (FIG. 3A), but all had very weak or no measurable neutralizing antibodies against heterologous RSV-B1 strain as measured by PRNT (FIG. 3B). Surprisingly, mice vaccinated with the glycosylated RMG did not develop RSV-neutralizing antibodies against either strain (as measured in the PRNT) after two immunizations (FIGS. 3A and B).

To get more complete information about the antibody responses to the two recombinant G proteins in mice, total anti-G binding antibody titers were measured by surface plasmon resonance based real-time kinetics assay (SPR) using REG or RMG proteins captured on SPR chip surface (FIGS. 4A and B, respectively). As can be seen, sera from the REG immunized mice demonstrated high total binding antibodies to the REG (FIG. 4A, red dots). Importantly, strong binding to the glycosylated RMG was also observed for the REG immunized mice sera (FIG. 4B, red dots). However, sera from mice immunized with the adjuvanted glycosylated RMG protein gave >10 fold lower binding to both REG and RMG proteins in SPR (FIGS. 4A and B, green dots).

REG Vaccination Generates Higher Diversity of the Antibody Immune Response Compared to RMG Vaccination To test which antigenic regions are recognized by antibodies generated following REG and RMG vaccination, a series of antigenic peptides derived from the N-terminus, CCD and C-terminus of the G protein were designed and tested in SPR. Serum samples from REG vaccinated mice showed strong binding to all G peptides, suggesting that REG induces a diverse antibody immune response that encompasses most of the RSV G protein (FIG. 4C). In contrast, sera from mice vaccinated with RMG generated antibodies that recognized peptides from the CCD and C-terminus, but not the N-terminus of RSV-G protein. In addition, the RMG-induced antibody titers were lower than those generated following REG vaccination for all peptides tested. These data suggested that the non-glycosylated RSV G protein can induce strong binding antibodies against more diverse epitopes of the G protein compared with the glycosylated RMG immunogen.

REG Immunization Provides Better Protection than RMG Against Both Homologous and Heterologous RSV Challenge To examine whether REG or RMG immunization could protect from homologous and heterologous RSV viral challenge, mice were intra-nasally (i.n.) infected with $1\times10^6$ pfu of either RSV A2 or RSV B1 virus strains 14 days after the second immunization with REG, RMG, F (positive control) and PBS (negative control) (FIG. 5A-B). Since both viruses are not lethal for mice, we measured viral loads in the lungs on day 4 post-challenge. Two log reduction in lung viral loads compared to mock (PBS) vaccinated control animals is considered good control of virus replication. The majority of F-vaccinated animals reduced viral loads completely after challenge with both RSV A2 and B1 strains (FIG. 5A-B, purple symbols). Among the REG vaccinated animals, seven out of eight mice completely protected from viral replication in the lungs and the eighth animal in each group showed >2 fold reduction in viral loads following challenge with either RSV A2 or B1 strains (FIG. 5A-B, red symbols). In contrast, RMG immunization conferred more variable protection and reduction of viral loads after homologous RSV A2 (2/8 animals protected) or heterologous RSV B1 (4/8 protected) virus challenge (FIG. 5A-B, green symbols).

The lack of detectable neutralizing antibodies in mice that were completely or partially protected from challenge suggested that protection was mediated by immunological functions not captured in the traditional RSV-PRNT, unlike the case in RSV F-immunized animals. A relationship plot between the individual mice anti-G binding serum antibody titers after the second immunization and lung viral loads after RSV challenge, (FIG. 5C) showed that anti-G binding antibody titers have statistically significant inverse correlation with lung viral loads against the homologous RSV A2 strain (FIG. 5C) ($r=-0.6248$; $p=0.0014$). In the case of RSV B1, a weaker inverse correlation was found between anti-G binding antibodies and lung viral loads ($r=-0.3961$; $p=0.0613$; data not shown).

Therefore, it was apparent that REG immunogen conferred better protective immunity than RMG against both homologous and heterologous RSV challenge, but the mechanisms of protection may include immune mechanisms not measured using a classical RSV PRNT.

Glycosylated RMG Induces Enhanced Pathology in the Lungs Following Virus Infection, while Nonglycosylated REG Protein Provides Protection from Lung Pathology Previous studies have suggested that vaccines based on RSV G protein can prime mice for enhanced lung pathology following RSV challenge that was associated with increased cytokine production and cellular infiltration due to eosinophils, neutrophils and NK cells (28-31) (32). Therefore, we investigated whether REG or RMG mice immunization leads to enhanced lung pathology following RSV challenge. The two RSV strains used in current study, RSV A2 and B1, are known to cause mild lung pathology in mice. Lungs were collected from RSV-infected animals and were analyzed by histopathology as described in materials and methods. At 2 days following virus challenge, lungs from PBS (control) vaccinated mice showed mild lung pathology after RSV infection (FIG. 6). Lungs from RMG-immunized mice demonstrated more cellular infiltrates and higher scores of perivasculitis and interstitial pneumonia than placebo (PBS) immunized mice following either homologous or heterologous RSV viral challenge. In contrast, REG immunized mice showed lung pathology scores that were lower compared to PBS immunized mice after infection with RSV A2. Surprisingly, scores were similarly low in REG immunized mice following challenge with RSV B1 virus even though these mice lacked serum neutralizing antibodies against RSV as measured in PRNT (FIG. 6A-B). In addition, cellular infiltrates in the lungs of PBS and REG immunized mice were composed mostly of lymphocytes with few eosinophils, while lungs in RMG immunized mice contained mostly eosinophils. Similar lung pathology was observed in animals on day 4 following RSV challenge (data not shown). These results suggest that nonglycosylated REG immunogen provides good protection from RSV mediated disease by control of lung viral loads and reduces lung disease, while the glycosylated RMG counterpart induces enhanced pathology in the lungs following RSV infection.

Cytokine Profile in Lungs of REG and RMG Immunized Mice Following Virus Challenge A hallmark of RSV vaccine-induced enhanced pathology in mice is the increase in cytokine expression and the development of a skewed Th2 response. Therefore, levels of Th1 or Th2 cytokines and chemokines were measured in lung homogenates of immunized mice following RSV infection (FIG. 7). IL-4, known to be important for the development of a Th2 response, was >100-fold higher in the lungs of RMG immunized mice compared to placebo (PBS), while IL-4 levels in REG immunized mice were comparable to the PBS control (FIG. 7A). IFN-γ, a Th1 cytokine, was only ~2 fold higher in RMG immunized mice than placebo or REG immunized mice (FIG. 7E). As a consequence, the ratio of Th2/Th1 (IL-4/IFNγ) cytokines was significantly higher in the lungs of mice immunized with RMG immunogen compared with placebo or REG immunized mice following RSV infection (FIG. 7I), IL-5, and IL-13, involved in eosinophil recruitment, airway hyper responsiveness and mucus production (29, 33), were found at significantly elevated levels in mice immunized with RMG compared to placebo, while in lungs from REG immunized mice these cytokines were at similar ranges as in the placebo control lungs (FIG. 7B-D). We also identified significant production of IL-6, a proinflammatory cytokine often associated with increased C-reactive protein (CRP) and elevation in body temperature. The chemokines Eotaxin, MCP-1 and MIP-1α, previously found to be involved in RSV induced enhanced lung pathology (34), were also observed at significantly higher levels in the lungs of RSV-challenged RMG-immunized mice compared with the REG-immunized or PBS control mice (FIG. 7F-H). The elevated levels of cytokines and chemokines in the RMG immunized mice following viral challenge seems to be immune mediated and were independent of lung viral loads following RSV viral challenge since similar or higher viral loads were observed in the PBS control mice (FIG. 5).

Together, this study demonstrated that RMG vaccination induced enhanced lung cellular infiltration, as measured by both histopathology and cytokine levels after RSV challenge and did not elicit strong protective immunity, while the REG vaccine did not induce enhanced pathology and conferred protection against both homologous and heterologous RSV strains even in the absence of a neutralizing antibody response.

Discussion

New efforts are under way to develop subunit vaccines against RSV that will provide protective immunity without the potential for disease enhancement as was observed in infants following vaccination with the formalin-inactivated. RSV (FI-RSV) vaccine in the 1960s (5, 35-37). Most recent RSV vaccine development efforts are focused on the F protein, which is more conserved among strains (3) and can be expressed in mammalian and insect cells (15, 16, 38, 39). The G attachment protein expressed on the virus surface also represents an important candidate for inclusion in RSV vaccines. However, glycosylated G protein expressed in mammalian cells or recombinant vaccinia virus expressing G protein was shown in mouse models to induce pulmonary eosinophilia upon RSV infection, mimicking the response seen with FI-RSV vaccine (33, 40, 41). Therefore, we decided to evaluate side by side the immunogenicity and safety of recombinant unglycosylated G protein ectodomain (amino acids 67-298) expressed in *E. coli* (REG) and a fully glycosylated G ectodomain produced in 293-Flp-In mammalian cells (RMG) in a mouse RSV-challenge model. The FI-RSV model was not included in the current study since it has been documented in previous studies, wherein the effect in immune responses, lung cytokines and pathology can be influenced by multiple viral proteins. Mice were vaccinated twice with low dose of REG or RMG (5 μg) in combination with the veterinary adjuvant Emulsigen (FIGS. 1-2). Two vaccinations with REG generated neutralizing antibodies against RSV A2 in 7/11 animals in PRNT. In contrast, the glycosylated RMG did not elicit neutralizing antibodies as measured in the PRNT (FIG. 3). Previous studies wherein glycosylated G protein was shown to be protective in mice typically used three vaccinations with ≥10 μg protein per dose. In this study, we gave only two vaccinations of a lower dose of the G proteins (5 μg) to differentiate the impact of glycosylation on virus neutralization and disease enhancement phenomenon after RSV infection of G-vaccinated animals. Total binding antibodies against the recombinant proteins (both REG and RMG) was measured by SPR and was found to be >10-fold higher in the REG immunized mice sera compared with sera from RMG vaccinated animals. Furthermore, REG immune sera contained antibodies against peptides spanning the entire G ectodomain, while RMG sera recognized more restricted targets in central conserved domain (CCD) and the C-terminus (FIG. 4C).

Homologous and heterologous protection was evaluated by measuring lung viral loads on day 4 after challenge with either RSV A2 (homologous) or RSV B1 (heterologous)

strains. Complete control of viral loads was observed in the majority of animals vaccinated with adjuvanted REG and challenged with either RSV strain. In contrast, the majority of RMG-vaccinated animals did not control virus replication after homologous or heterologous virus challenge (FIG. 5). The correlate of protection needs to be further investigated as classical PRNT did not measure neutralizing antibodies in all animals that were subsequently protected against challenge. There were animals with low or no serum neutralization titers that controlled lung viral loads very well. This was most evident in animals challenged with the heterologous RSV B1 strain. It has been shown before that anti-G antibodies may neutralize virus in vivo but not in the in vitro PRNT (25). Cell mediated immunity may also play a role in virus clearance after RSV challenge. However, previous studies showed that BALB/c mice immunized with either FI-RSV or recombinant vaccinia virus that expresses the RSV G attachment protein generated RSV specific $CD4^+$ T cells but did not prime $CD8^+$ T cells (42, 43). In our study, a strong inverse correlation was observed between the total anti-G binding serum antibody titers (measured by SPR) and lung viral loads after RSV challenge. Therefore, it is likely that some anti-G binding antibodies that are protective in vivo do not neutralize RSV very well in the PRNT as was found for anti-G MAb 131-2G (25).

Figures 6A, 6B:
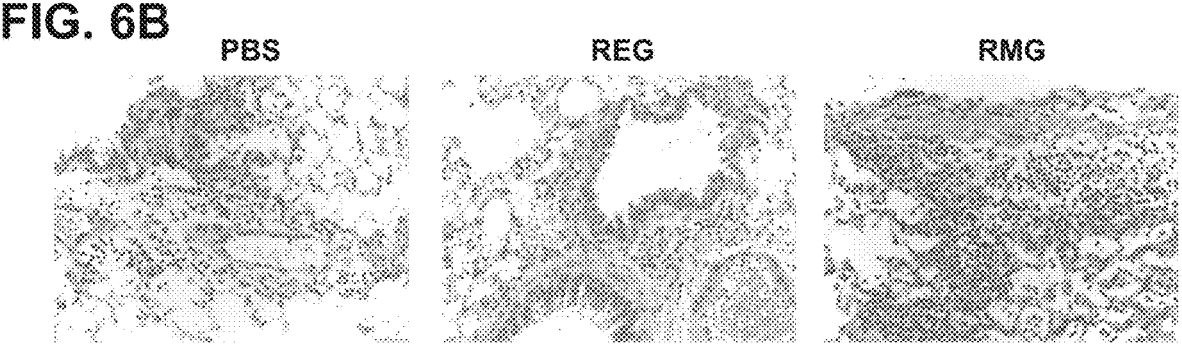
FIGS. 6A and 6B show histopathology analysis of lungs from REG and RMG immunized mice after virus challenge: REG immunization protected from lung disease, while RMG immunization resulted in perivasculitis and lung cellular infiltrates after challenge (enhanced disease/pathology). Lungs collected 2 days post-challenge with RSV-A2 or RSV-B1 were stained with hematoxylin and eosin (H-E) and scored for inflammation in bronchioles, near veins (vascular), and alveoli.

An important safety aspect of subunit and non-replicating candidate vaccines against RSV is its potential to enhance the occurrence of severe disease after infection. Elevated levels of Th2 cytokines were implicated in the enhanced cellular infiltration predominated by eosinophils. The RSV G glycoprotein in particular has been implicated as an RSV antigen that promotes Th2 $CD4^+$ T lymphocytes and induces eosinophilic infiltrates in the lungs after RSV challenge (28, 29, 33, 44-47). Therefore, lungs were isolated two days or four days after RSV challenge and evaluated by histopathology and quantification of cytokines and chemokines. It was observed that the glycosylated RMG vaccinated animals demonstrated significant lung histopathology after either RSV-A2 or RSV-B1 challenge (FIG. 6). Furthermore, a Th2-dominant cytokine response was measured in the lungs of all RMG vaccinated RSV-Challenged animals, and chemokine levels (Eotaxin, MCP-1 and MIP-2α) were elevated as well (FIG. 7). In addition, elevated IL-6, a known proinflammatory cytokine that is associated with upregulation of C-reactive protein and fever was found in the lungs of RMG-vaccinated animals. Importantly, the E. coli derived REG-vaccinated animals had no evidence of an increase in lung cellular infiltrates compared with PBS control animals and no elevation of Th2 cytokines and chemokines. The IL4/IFNγ ratios were significantly higher in the RMG vaccinated group compared with the PBS and REG vaccinated animals following virus challenge. The elevated levels of cytokines and chemokines and enhanced lung pathology in the RMG immunized mice following viral challenge seems to be immune mediated and was independent of lung viral loads following RSV viral challenge. Similar or higher viral loads were observed in the PBS control mice that showed lower cytokine levels and less lung pathology. The combination of low virus neutralizing activity and enhanced lung pathology observed in the RMG vaccinated animals is reminiscent of the findings in children and animals vaccinated with FI-RSV. The lack of enhanced lung pathology after REG vaccination is a very important finding that is an absolute requirement for further development of any RSV G based vaccine.

Both purified recombinant G proteins were identical in terms of their primary amino acid sequence and were administered in combination with the same adjuvant, Emulsigen. Therefore, the observed increase in Th2 cytokines IL-5, IL-13) and multiple chemokines in the lungs of RMG-vaccinated animals (but not REG-vaccinated animals) after RSV challenge could not be simply attributed to binding of the CX3C motif within CCD to the CX3CR1 (fractalkine receptor) on several cell types, as previously suggested (48). Instead, the enhanced Th2 and chemokine levels could possibly be induced by the high level of O-linked sugars characteristic of mammalian cell expressed glycosylated RMG and also of the native virus-associated G attachment protein. A role for processing by different glycosylation specific antigen presenting cell subsets that could influence the subsequent Th2 vs. Th1 cytokines has been reported and should be further investigated (49, 50).

Our findings are in agreement with previous studies using E. coli produced fusion protein, BBG2Na that contained the central conserved region of A2 G gene (amino acids 130-230) (G2Na) fused to the albumin-binding domain of streptococcal protein G protein (BB) formulated with aluminum adjuvant (51-54). In comparison with BBG2Na, our REG encompass the entire G-ectodomain with no "foreign" sequences or fusion protein that may influence the immune response to the irrelevant target (BB rather than G2Na) during vaccinations. Most of the studies with BBG2Na used 20 μg of the vaccine in a series of three vaccinations. In contrast, in our study, only two vaccinations with 5 μg REG protein/dose elicited strong protection. Also, REG-immunization induced antibodies with diverse epitope repertoire that recognized multiple targets in the G protein spanning the N-terminus, central conserved domain, and C-terminus of the protein (FIG. 4C and data not shown). We will continue to investigate the contribution of antibodies against different parts of the G protein in homologous and heterologous protection against RSV infection.

In summary, our study for the first time compared side by side fully glycosylated and unglycosylated G proteins for immunogenicity and safety in a murine RSV challenge model. It also provided data supporting the feasibility of developing simple recombinant RSV G-based vaccine produced in E. coli expression system. This immunogen is unlikely to induce the Th2/Th1 imbalance observed after vaccination with fully glycosylated G protein that resulted in significant cellular infiltration and lung pathology. Moreover, when combined with the appropriate adjuvant it elicits protective antibodies against both homologous and heterologous RSV challenge. The bacterial expression system for G protein based vaccine provides economical alternative to cell-based subunit vaccines as was previously demonstrated for influenza HA1 proteins from multiple virus strains (21, 55-57), that should be evaluated alone or in combination with F-subunit vaccines for effective protection against RSV disease.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

REFERENCE TO A SEQUENCE LISTING

This application includes a Sequence Listing as a text file named "Sequence.txt" created Sep. 21, 2017, and containing 45,056 bytes. The material contained in this text file is incorporated by reference in its entirety for all purposes.

REFERENCES

1. Zhou H, Thompson W W, Viboud C G, Ringholz C M, Cheng P Y, Steiner C, Abedi G R, Anderson L J, Brammer L, Shay D K. 2012. Hospitalizations associated with influenza and respiratory syncytial virus in the United States, 1993-2008. Clin Infect Dis 54:1427-1436.
2. Hertz M I, Englund J A, Snover D, Bitterman P B, McGlave P B. 1989. Respiratory syncytial virus-induced acute lung injury in adult patients with bone marrow transplants: a clinical approach and review of the literature. Medicine 68:269-281.
3. Graham B S. 2011. Biological challenges and technological opportunities for respiratory syncytial virus vaccine development. Immunol Rev 239:149-166.
4. Thompson W W, Shay D K, Weintraub E, Brammer L, Cox N, Anderson Fukuda K. 2003. Mortality associated with influenza and respiratory syncytial virus in the United States. JAMA 289:179-186.
5. Kim H W, Canchola. J G, Brandt C D, Pyles G, Chanock R M, Jensen K, Parrott R H, 1969, Respiratory syncytial virus disease in infants despite prior administration of antigenic inactivated vaccine. Am J Epidemiol 89:422-434.
6. Murphy B R, Prince G A, Walsh E E, Kim V, Parrott R H, Hemming V G, Rodriguez W J, Chanock R M. 1986. Dissociation between serum neutralizing and glycoprotein antibody responses of infants and children who received inactivated respiratory syncytial virus vaccine. J Clin Microbiol 24:197-202.
7. Murphy B R, Walsh E E. 1988, Formalin-inactivated respiratory syncytial virus vaccine induces antibodies to the fusion glycoprotein that are deficient in fusion-inhibiting activity. J Clin Microbiol 26:1595-1597.
8. Polack F P, Teng M N, Collins P L, Prince G A, Exner M, Regele H, Lirman D D, Rabold R, Hoffman S J, Karp C L, Kleeberger S R, Wills-Karp M, Karron R A. 2002. A role for immune complexes in enhanced respiratory syncytial virus disease. J Exp Med 196:859-865.
9. Graham B S, Henderson G S, Tang Y W, Lu X, Neuzil K M, Colley D G. 1993. Priming immunization determines T helper cytokine mRNA expression patterns in lungs of mice challenged with respiratory syncytial virus. J Immunol 151:2032-2040.
10. Connors M, Kulkarni A B, Firestone C Y, Holmes K L, Morse H C, 3rd, Sotnikov A V, Murphy B R. 1992. Pulmonary histopathology induced by respiratory syncytial virus (RSV) challenge of formalin-inactivated RSV-immunized BALB/c mice is abrogated by depletion of CD4+ T cells. J Virol 66:7444-7451.
11. Karron R A, Wright P F, Belshe R B, Thumar B, Casey R, Newman F, Polack F P, Randolph V B, Deafly A, Hackell J, Gruber W, Murphy B R, Collins P L. 2005. Identification of a recombinant live attenuated respiratory syncytial virus vaccine candidate that is highly attenuated in infants. J Infect Dis 191:1093-1104.
12. Falsey A R, Walsh E E. 1996. Safety and immunogenicity of a respiratory syncytial virus subunit vaccine (PFP-2) in ambulatory adults over age 60. Vaccine 14:1214-1218.
13. Langley J M, Sales V, McGeer A, Guasparini. R, Predy G, Meekison W, Li M, Capellan J, Wang E. 2009. A dose-ranging study of a subunit Respiratory Syncytial Virus subtype A vaccine with and without aluminum phosphate adjuvantation in adults > or =65 years of age. Vaccine 27:5913-5919.
14. Ofek G, Guenaga F J, Schief W R, Skinner J, Baker D, Wyatt R, Kwong P D. 2010. Elicitation of structure-specific antibodies by epitope scaffolds. Proc Natl. Acad Sci USA 107:17880-17887.
15. Swanson K A, Balabanis K, Xie Y, Aggarwal Y, Palomo C, Mas V, Metrick C, Yang H, Shaw C A, Melero J A. Dormitzer P R. Carfi A. 2014. A monomeric uncleaved respiratory syncytial virus F antigen retains prefusion-specific neutralizing epitopes. Virol 88:11802-11810.
16, McLellan J S, Chen M, Leung S, Graepel K W, Du X, Yang Y, Zhou T, Bata U, Yasuda E, Beaumont T, Kumar A, Modjarrad K, Zheng Z, Zhao M, Xia N, Kwong P D, Graham B S. 2013. Structure of RSV fusion glycoprotein trimer bound to a prefusion-specific neutralizing antibody. Science 340:1113-1117.
17. Power U F, Nguyen T N, Rietveld E, de Swart R L, Groen J, Osterhaus A D, de Groot R, Corvaia N, Beck A, Bouveret-Le-Cam N, Bonnefoy J Y. 2001. Safety and immunogenicity of a novel recombinant subunit respiratory syncytial virus vaccine (BBG2Na) in healthy young adults. J Infect Dis 184:1456-1460.
18. de Waal L, Power U F, Yuksel S, van Amerongen G, Nguyen T N, Niesters H G, de Swart R L, Osterhaus A D. 2004. Evaluation of BBG2Na in infant macaques: specific immune responses after vaccination and RSV challenge. Vaccine 22:915-922.
19. Khurana S, Larkin C. Verma S, Joshi M B, Fontana J, Steven A C, King L R, Manischewitz J, McCormick W, Gupta R K, Golding H. 2011. Recombinant HA1 produced in E. coli forms functional oligomers and generates strain-specific SRID potency antibodies for pandemic influenza vaccines. Vaccine 29:5657-5665.
20. Lu H, Khurana S, Verma N, Manischewitz J, King L, Beigel J H, Golding H. 2011. A rapid. Flp-In system for expression of secreted H5N1 influenza hemagglutinin vaccine immunogen in mammalian cells. PLoS One 6:e17297.
21. Khurana S, Verma S, Verma N, Crevar C J, Carter D M, Manischewitz J, King L R, Ross T M, Golding H. 2010. Bacterial HA1 vaccine against pandemic H5N1 influenza virus: evidence of oligomerization, hemagglutination, and cross-protective immunity in ferrets. J Virol 85:1246-1256.
22. Fuentes S, Crim R L, Beeler J, Ting M N, Golding H, Khurana S. 2013. Development of a simple, rapid, sensitive, high-throughput luciferase reporter based microneutralization test for measurement of virus neutralizing antibodies following Respiratory Syncytial Virus vaccination and infection. Vaccine 31:3987-3994.
23. Satake M, Coligan J E, Elango N, Norrby E, Venkatesan S. 1985. Respiratory syncytial virus envelope glycoprotein (G) has a novel structure. Nucleic Acids Res 13:7795-7812.
24. Anderson L J, Hierholzer J C, Stone Y O, Tsou C, Fernie B F. 1986. Identification of epitopes on respiratory syncytial virus proteins by competitive binding immunoassay. J Clin Microbiol 23:475-480.
25. Anderson L J, Bingham P, Hierholzer J C. 1988. Neutralization of respiratory syncytial virus by individual and mixtures of F and G protein monoclonal antibodies. J Virol 62:4232-4238.
26. Choi Y, Mason C S, Jones L P, Crabtree J, Jorquera P A, Tripp R A. 2012. Antibodies to the central conserved region of respiratory syncytial virus (RSV) G protein 26. block RSV G protein CX3C-CX3CR1 binding and cross-neutralize RSV A and B strains. Viral Immunol 25:193-203.
27. Jorquera P A, Choi Y, Oakley K E, Powell T J, Boyd J G, Palath N, Haynes L M, Anderson L J, Tripp R A. 2013. Nanoparticle vaccines encompassing the respiratory syncytial virus (RSV) G protein CX3C chemokine motif induce robust immunity protecting from challenge and disease. PLoS One 8:e74905.
28. Johnson T R, Johnson J E, Roberts S R, Wertz G W, Parker R A, Graham B S. 1998. Priming with secreted glycoprotein G of respiratory syncytial virus (RSV) augments interleukin-5 production and tissue eosinophilia after RSV challenge. J Virol 72:2871-2880.
29. Johnson T R, Graham B S. 1999. Secreted respiratory syncytial virus G glycoprotein induces interleukin-5 (IL-5), IL-13, and eosinophilia by an IL-4-independent mechanism. J Virol 73:8485-8495.
30. Tripp R A, Moore D, Jones L, Sullender W, Winter J, Anderson L J. 1999. Respiratory syncytial virus G and/or SH protein alters Th1 cytokines, natural killer cells, and neutrophils responding to pulmonary infection in B ALB/c mice. J Virol 73:7099-7107.
31. Tripp R A, Moore D, Winter J, Anderson L J. 2000. Respiratory syncytial virus infection and G and/or SH protein expression contribute to substance P, which mediates inflammation and enhanced pulmonary disease in BALB/c mice. J Virol 74:1614-1622.
32. Tripp R A, Moore D, Anderson L J. 2000. TH(1)- and TH(2)-TYPE cytokine expression by activated t lymphocytes from the lung and spleen during the inflammatory response to respiratory syncytial virus. Cytokine 12:801-807.
33. Castilow E M, Meyerholz D K, Varga S M. 2008. IL-13 is required for eosinophil entry into the lung during respiratory syncytial virus vaccine-enhanced disease. J Immunol 180:2376-2384.
34. Jafri H S, Chavez-Bueno S, Mejias A, Gomez A M, Rios A M, Nassi S S, Yusuf M, Kapur P, Hardy R D, Hatfield J, Rogers B B, Krisher K, Ramilo O. 2004. Respiratory syncytial virus induces pneumonia, cytokine response, airway obstruction, and chronic inflammatory infiltrates associated with long-term airway hyperresponsiveness in mice. J Infect Dis 189:1856-1865.
35. Kapikian A Z, Mitchell R H, Chanock R M, Shvedoff R A, Stewart C E. 1969. An epidemiologic study of altered clinical reactivity to respiratory syncytial (RS) virus infection in children previously vaccinated with an inactivated RS virus vaccine. Am J Epidemiol 89:405-421.
36. Fulginiti V A, Eller J J, Sieber O F, Joyner J W, Minamitani M, Meiklejohn G. 1969. Respiratory virus immunization. I. A field trial of two inactivated respiratory virus vaccines; an aqueous trivalent parainfluenza virus vaccine and an alum-precipitated respiratory syncytial virus vaccine. Am J Epidemiol 89:435-448.
37. Chin J, Magoffin R L, Shearer L A, Schieble J H, Lennette E H. 1969. Field evaluation of a respiratory syncytial virus vaccine and a trivalent parainfluenza virus vaccine in a pediatric population. Am J Epidemiol 89:449-463.
38. Lee J S, Kwon Y M, Hwang H S, Lee Y N, Ko E J, Yoo S E, Kim M C, Kim K R, Cho M K, Lee Y T, Lee Y R, Quan F S, Kang S M. 2014. Baculovirus-expressed virus-like particle vaccine in combination with DNA encoding the fusion protein confers protection against respiratory syncytial virus. Vaccine 32:5866-5874.
39. Raghunandan R, Lu H, Zhou B, Xabier M G, Massare M J, Flyer D C, Fries L F, Smith G E, Glenn G M. 2014, An insect cell derived respiratory syncytial virus (RSV) F nanoparticle vaccine induces antigenic site II antibodies and protects against RSV challenge in cotton rats by active and passive immunization. Vaccine 32:6485-6492.
40. Openshaw P J, Clarke S L, Record F M. 1992. Pulmonary eosinophilic response to respiratory syncytial virus infection in mice sensitized to the major surface glycoprotein G. Int Immunol. 4:493-500.
41. Everard M L, Swarbrick A, Wrightham M, McIntyre J, Dunkley C, James P D, Sewell H E, Milner A D. 1994. Analysis of cells obtained by bronchial lavage of infants with respiratory syncytial virus infection. Arch Dis Child 71:428-432.
42. Olson M R, Varga S M. 2007. CD8 T cells inhibit respiratory syncytial virus (RSV) vaccine-enhanced disease. J Immunol 179:5415-5424.
43. Olson M R, Hartwig S M, Varga S M. 2008. The number of respiratory syncytial virus (RSV)-specific memory CD8 T cells in the lung is critical for their ability to inhibit RSV vaccine-enhanced pulmonary eosinophilia. J Immunol 181:7958-7968.
44. Alwan W H, Openshaw P J. 1993. Distinct patterns of T- and B-cell immunity to respiratory syncytial virus induced by individual viral proteins. Vaccine 11:431-437.
45. Atwan W H, Record F M, Openshaw P J. 1993. Phenotypic and functional characterization of T cell lines specific for individual respiratory syncytial virus proteins. J Immunol 150:5211-5218.
46. Hancock G E, Speelman D J, Heers K, Borten E, Smith J, Cosco C. 1996. Generation of atypical pulmonary inflammatory responses in BALB/c mice after immunization with the native attachment (G) glycoprotein of respiratory syncytial virus. J Virol 70:7783-7791.
47. Srikiatkhachorn A, Braciale T J. 1997. Virus-specific memory and effector T lymphocytes exhibit different cytokine responses to antigens during experimental murine respiratory syncytial virus infection. J Virol 71:678-685.
48. Haynes L M, Jones L P, Barskey A, Anderson L J, Tripp R A. 2003. Enhanced disease and pulmonary eosinophilia associated with formalin-inactivated respiratory syncytial virus vaccination are linked to G glycoprotein CX3C-CX3CR1 interaction and expression of substance P. J Virol 77:9831-9844.
49. Rissoan M C, Soumelis V, Kadowaki N, Grouard G, Briere F, de Waal Malefyt R, Liu Y J. 1999. Reciprocal control of T helper cell and dendritic cell differentiation. Science 283:1183-1186.
50. Johnson T R, McLellan J S, Graham B S. 2012. Respiratory syncytial virus glycoprotein G interacts with DC-SIGN and L-SIGN to activate ERK1 and ERK2. J Virol 86:1339-1347.
51. Power U F, Plotnicky-Gilquin H, Huss T, Robert A, Trudel M, Stahl S, Uhlen M, Nguyen T N, Binz H. 1997. Induction of protective immunity in rodents by vaccination with a prokaryotically expressed recombinant fusion protein containing a respiratory syncytial virus G protein fragment. Virology 230:155-166.
52. Plotnicky-Gilquin H, Huss T, Aubry J P, Haeuw J F, Beck A, Bonnefoy J Y, Nguyen T N, Power U F. 1999. Absence of lung immunopathology following respiratory syncytial virus (RSV) challenge in mice immunized with a recombinant RSV G protein fragment. Virology 258:128-140.
53. Corvaia N, Tournier P, Nguyen T N, Haeuw J F, Power U F, Binz H, Andreoni C. 1997. Challenge of BALB/c mice with respiratory syncytial virus does not enhance the Th2 pathway induced after immunization with a recombinant G fusion protein, BBG2NA, in aluminum hydroxide. J Infect Dis 176:560-569.
54. Power U F, Plotnicky H, Blaecke A, Nguyen T N. 2003. The immunogenicity, protective efficacy and safety of BBG2Na, a subunit respiratory syncytial virus (RSV) vaccine candidate, against RSV-B. Vaccine 22:168-176.
55. Khurana S, Verma S, Verma N, Crevar C J, Carter D M, Manischewitz J, King L R, Ross T M, Golding H. 2010. Properly folded bacterially expressed H1N1 hemagglutinin globular head and ectodomain vaccines protect ferrets against H1N1 pandemic influenza virus. PLoS ONE 5:e11548.
56. Verma S, Dimitrova M, Munjal A, Fontana J, Crevar C J, Carter D M, Ross T M, Khurana S, Golding H. 2012. Oligomeric recombinant H5 HA1 vaccine produced in bacteria protects ferrets from homologous and heterologous wild-type H5N1 influenza challenge and controls viral loads better than subunit H5N1 vaccine by eliciting high-affinity antibodies. J Virol 86:12283-12293.
57. Khurana S, Coyle E M, Verma S. King L K, Manischewitz J, Crevar C J, Carter D M, Ross T M, Golding H. 2014. H5 N-terminal beta sheet promotes oligomerization of H7-HA1 that induces better antibody affinity maturation and enhanced protection against H7N7 and H7N9 viruses compared to inactivated influenza vaccine. Vaccine.

SEQUENCE LISTING

SEQ ID NO: 1 RSV-A2 ectodomain (67-298) codon optimized sequence for E. coli:
CATAAAGTCACCCCGAYCCACGGCGATTATCCAGGATGCCACCTCTCAAATCAAAAA
CACCACGCCGACGTACCTGACCCAGAATCCGCAACTGGGCATTTCACCGTCGAACCC
GTCAGAAATCACCTCGCAGATTACCACGATCCTGGCAAGCACCACGCCGGGTGTCA
AAAGCACGCTGCAATCTACCACGGTGAAAACCAAAAATACCACGACCACGCAGACC
CAACCGAGCAAACCGACCACGAAACAGCGTCAAAATAAACCGCCGTCTAAACCGAA
CAATGATTTTCACTTCGAAGTGTTTAACTTCGTTCCGTGCAGTATTTGTTCCAACAAT
CCGACCTGCTGGGCCATTTGTAAACGCATCCCGAACAAAAAACCGGGCAAGAAAAC
CACGACCAAACCGACGAALAAACCGACCCTGAAAACGACCAAAALAGACCCGAAA
CCGCAGACGACCAAAAGCAAAGAAGTGCCGACGACCAAACCGACGGAAGAACCGA
CCATTAACACGACCAAAACCAATATTATCACGACCCTGCTGACCTCCAACACGACCG
GCAATCCGGAACTGACCTCACAGATGGAAACGTTCCATTCGACCAGCTCTGAAGGT
AATCCGAGCCCGTCTCAGGTCAGCACGACCTCCGAATACCCGAGCCAGCCGTCTTCT
CCGCCGAATACCCCGCGTCAG SEQ ID NO: 2 RSV-A2 ectodomain (67-298) protein sequence:
HKVTPTTAIIQDATSQIKNTTPTYLTQNPQLGISPSNPSEITSQITTILASTTPGVKSTLQSTTVKTKNTTTTQTQP
SKPTTKQRQNKPPSKPNNDFHFEVFNFVPCSICSNNPTCWAICKRIP
NKKPGKKTTTKPTKKPTLKTTKKDPKPQTTKSKEVPTTKPTEEPTINTTKTNIITTLLTSN
TTGNPELTSQMETFHSTSSEGNPSPSQVSTTSEYPSQPSSPPNTPRQ

RSV-F PEPTIDE SEQUENCES

| SEQ ID NO: | Amino Acid No | Sequence |
|---|---|---|
| 3 | 1-34 | MELLILKANAITTILTAVTFCEASGQNITEEFYQ |
| 4 | 23-74 | ASGQNITEEFYQSTCSAVSKGYLSALRTGWYTSVITIELSNIKKNKCNGTDA |
| 5 | 101-157 | PATNNRARRELPRFMNYTLNNAKKTNVTLSKKRKRRFLGFLLGVGSAIASGVAVSKV |
| 6 | 82-115 | ELDKYKNAVTELQLLMQSTPATNNRARPELPRFM |
| 7 | 101-121 | PATNNRARRELPRFMNYTLNN |
| 8 | 137-155 | FLGFLLGVGSAIASGVAVS |
| 9 | 174-203 | TNKAVVSLSNGVSVLTSKVLDLKNYIDKQL |
| 10 | 176-240 | KAVVSLSNGVSVLTSKVLDLKNYIDKQLLPIVNKQSCSIS NIETVIEFQQKNNRLLEITREFSVN |
| 11 | 190-233 | SKVLDLKNYIDKQLLPIVNKQSCSISNIETVIEFQQKNNRLLEI |
| 12 | 195-240 | LKNYIDKQLLPIVNKQSCSISNIETVIEFQQKNNRLLEITREFSVN |
| 13 | 216-244 | NIETVIEFQQKNNRLLEITREFSVNAGVT |
| 14 | 234-287 | TREFSVNAGVTTPVSTYMLTNSELLSLINDMPITNDQKKLMSNNVQIVRQQSYS |
| 15 | 250-273 | YMLTNSELLSLINDMPITNDQKKL |
| 16 | 310-368 | DTPCWKLHTSPLCTTNTKEGSNICLTRTDRGWYCDNAGSVSFFPQAETCKVQSNRVFCD |
| 17 | 341-353 | WYCDNAGSVSFFPQAETC |
| 18 | 371-400 | NSLTLPSEVNLCNVDIFNPKYDCKIMTSKT |
| 19 | 425-450 | SNKNRGIIKTFSNGCDYVSNKGVDTV |
| 20 | 443-461 | SNKGVDTVSVGNTLYYVNK |
| 21 | 475-521 | INFYDPLVFPSDEFDASISQVNEKINQSLAFIRKSDELLHNVNAVKS |
| 22 | 471-493 | GEPIINFYDPLVFPSDEFDASIS |
| 23 | 497-521 | EKINQSLAFIRKSDELLHNVNAVKS |
| 24 | 552-572 | ARSTPVTLSKDQLSGINNIAF |

RSV-G PEPTIDE SEQUENCES

| SEQ ID NO | Amino Acid No | Sequence |
|---|---|---|
| 25 | 33-61 | LNLKSVAQITLSILAMIISTSLIIAAIIF |
| 26 | 66-90 | NHKVTPTTAIIQDATSQIKNTTPTY |
| 27 | 90-110 | YLTQNPQLGISPSNPSEITSQ |
| 28 | 129-152 | TTVKTKNTTTTQTQPSKPTTKQRQ |
| 29 | 148-178 | TTKQRQNKPPSKPNNDFHFEVFNFVPCSICS |
| 30 | 169-207 | NFVPCSICSNNPTCWAICKRIPNKKPGKKTTTKPTKKPT |

| | | |
|---|---|---|
| 31 | 236-263 | INTTKTNIITTLLTSNTTGNPELTSQME |
| 32 | 245-274 | TTLLTSNTTGNPELTSQMETFHSTSSEGNP |
| 33 | 263-298 | ETFHSTSSEGNPSPSQVSTTSEYPSQPSSPPNTP |

SEQ ID NO: 38 RSV-A2 F codon optimized sequence for *E. coli*:
ATGGAACTGCTGATTCTGAAAGCCAACGCATTTACCACGATTCTGACCGCTGTTACCTTCTGTTTCGCCTCGGGC
CAAAATATCACGGAAGAATTTTATCAGAGTACCTGCTCCGCAGTTTCAAAAGGCTATCTGAGCGCTCTGCGTACC
GGTTGGTACACGTCGGTGATCACCATTGAACTGAGCAACATTAAAAAGAACAAGTGTAATGGCACGGATGCCAAA
ATCAAGCTGATTAAACAGGAACTGGACAAGTACAAGAACGCAGTTACCGAACTGCAGCTGCTGATGCAAAGCACC
AATGTTACGCTGTCCAAAAAGCGCAAACGTCGCTTTCTGGGCTTCCTGCTGGGTGTGGGTAGCGCCATTGCCAGC
GGCGTTGCAGTCTCTAAAGTGCTGCATCTGGAAGGTGAAGTTAACAAAATCAAGTCTGCGCTGCTGAGTACGAAC
AAAGCCGTGGTTTCCCTGTCAAATGGTGTGTCCGTTCTGACCTCAAAAGTGCTGGATCTGAAGAATTATATCGAC
AAACAGCTGCTGCCGATTGTGAACAAGCAATCGTGCAGCATCTCTAACATCGAAACGGTTATCGAATTTCAGCAG
AAAAACAATCGTCTGCTGGAAATCACCCGTGATTTTTCGGTTAACGCCGGTGTCACCACGCCTGTGAGCACGTAT
ATGCTGACCAATTCGGAACTGCTGAGCCTGATCAACGATATGCCGATTACCAATGACCAGAAAAAGCTGATGTCG
AACAATGTTCAAATTGTCCGTCAGCAAATTACTCCATCATGAGCATTATCAAAGAAGAAGTTCTGGCGTATGTC
GTGCAGCTGCCGCTGTACGGCGTCATTGATACGCCGTGCTGGAAGCTGCACACCTCTCCGCTGTGTACCACGAAC
ACCAAAGAAGGTAGTAATATTTGCCTGACCCGTACGGATCGCGGCTGGTATTGTGACAACGCGGGTTCAGTTTCG
TTTTTCCCGCAGGCCGAAACCTGCAAAGTGCAAAGCAACCGTGTGTTTTGCGATACGATGAACAGCCTGACCCTG
CCGAGTGAAGTCAACCTGTGCAATGTGGATATTTTCAATCCGAAATACGACTGTAAGATCATGAGCCAGTAAAACG
GATGTTAGCTCTAGTGTCATCACCTCCCTGGGCGCGATTGTGTCATGCTATGGTAAAACCAAGTGTACGGCCAGC
AACAAGAATCGCGGCATTATCAAAACCTTTTCTAACGGTTGCGATTACGTTAGTAATAAAGGCGTCGACACGGTC
TCTGTGGGTAACACCCTGTATTACGTCAATAAACAGGAAGGCAAGAGTCTGTATGTGAAAGGTGAACCGATTATC
AACTTTTACGATCCGCTGGTCTTTCCGTCTGATGAATTTGACGCAAGCATCTCTCAGGTGAACGAAAAGATTAAT
CAATCCCTGGCTTTCATCCGTAAATCAGACGAACTGCTGCATAACGTGAATGCGGTTAAAAGCACCACGAATATC
ATGATTACCACGATTATCATTGTCATCATTGTGATCCTGCTGTCCCTGATTGCAGTGGGCCTGCTGCTGTATTGT
AAAGCTCGCTCAACGCCGGTGACGCTGAGCAAAGACCAACTGTCGGGTATCAATAACATCGCATTTAGCAAC SEQ ID NO: 39 RSV-A2 F protein sequence:
MELLILKANAITTILTAVTFCFASGQNITEEFYQSTCSAVSKGYLSALRTGWYTSVITIELSNIKKNKCNGTDAKIK
LIKQELDKYKNAVTELQLLMQSTPATNNRARRELPRFMNYTLNNAKKTNVTLSKKRKRRFLGFLLGVGSAIASGVAV
SKVLHLEGEVNKIKSALLSTNKAVVSLSNGVSVLTSKVLDLKNYIDKQLLPIVNKQSCSISNIETVIEFQQKNNRLL
EITREFSVNAGVTTPVSTYMLTNSELLSLINDMPITNDQKKLMSNNVQIVRQQSYSIMSIIKEEVLAYVVQLPLYGV
IDTPCWKLHTSPLCTTNTKEGSNICLTRTDRGWYCDNAGSVSFFPQAETCKVQSNRVFCDTMNSLTLPSEVNLCNVD
IFNPKYDCKIMTSKTDVSSSVITSLGAIVSCYGKTKCTASNKNRGIIKTFSNGCDYVSNKGVDTVSVGNTLYYVNKQ
EGKSLYVKGEPIINFYDPLVFPSDEFDASISQVNEKINQSLAFIRKSDELLHNVNAVKSTTNIMITTIIIVIIVILL
SLIAVGLLLYCKARSTPVTLSKDQLSGINNIAFSN SEQ ID NO: 40 RSV-A2 F Ectodomain (23-524) protein sequence:
ASGQNITEEFYQSTCSAVSKGYLSALRTGWYTSVITIELSNIKKNKCNGTDAKIKLIKQELDKYKNAVTELQLLMQS
TPATNNRARRELPRFMNYTLNNAKKTNVTLSKKRKRRFLGFLLGVGSAIASGVAVSKVLHLEGEVNKIKSALLSTNK
AVVSLSNGVSVLTSKVLDLKNYIDKQLLPIVNKQSCSISNIETVIEFQQKNNRLLEITREFSVNAGVTTPVSTYMLT
NSELLSLINDMPITNDQKKLMSNNVQIVRQQSYSIMSIIKEEVLAYVVQLPLYGVIDTPCWKLHTSPLCTTNTKEGS
NICLTRTDRGWYCDNAGSVSFFPQAETCKVQSNRVFCDTMNSLTLPSEVNLCNVDIFNPKYDCKIMTSKTDVSSSVI
TSLGAIVSCYGKTKCTASNKNRGIIKTFSNGCDTVSNKGVDTVSVGNTLYYVNKQEGKSLTVKGEPIINFYDPLVFP
SDEFDASISQVNEKINQSLAFIRKSDELLHNVNAVKSTTN SEQ ID NO: 41 RSV-B1 ectodornain (67-299) codon optimized sequence for *E. coli*:
CATAAAGTTACCCTGACCACGGTGACGGTTCAGACCATTAAAAACCACACCGAGAAAAACATCACCACCTACCTGAC
CCAAGTTCCGCCGGAACGCGTCAGCTCTAGLAAACAGCCGACCACGACCAGCCCGATTCATACCAACTCAGCGACGA
CCTCGCCGAATACGAAATCTGAAACCCATCACACGACCGCCCAAACCAAAGGCCGTACGACCACGAGTACGCAGACC
AACAAACCGTCCACCAAACCGCGCCTGAAAAATCCGCCGAAAAAACCGAAAGATGACTATCACTTCGAAGTCTTTAA
CTTCGTGCCGTGCAGCATTTGTGGTAACAATCAGCTGTGCAAATCAATTTGTAAAACCATCCCGTCGAATAAACCGA
AGAAAAAACCGACGATCAAACCGACCAACAAACCGACCACGAAAACCACGAATAAACGTGATCCGAAAACCCCGGCA
AAAACCACCAAGAAAGAAACCACGACCAACCCGACGAAAAAACCGACCCTGACGACCACGGAACGCGATACGTCGAC
CAGCCAATCTACCGTCCTGGACACCACGACCCTGGAACATACCATTCAGCAACAGAGTCTGCACTCCACGACCCCGG
AAAACACGCCGAATAGCACCCAGACCCCGACCGCAAGCGAACCGAGCACCAGCAACTCCACCCAAAACACCCAATCC
CACGCA SEQ ID NO: 42 RSV-B1 ectodomain (67-299) protein sequence:
HKVTLTTVTVQTIKNHTEKNITTYLTQVPPERVSSSKQPTTTSPIHTNSATTSPNTKSETHHTTAQTKGRTTTSTQT
NKPSTKPRLKNPPKKPKDDYHFEVFNFVPCSICGNNQLCKSICKTIPSNKPKKKPTIKPTNKPTTKTTNKRDPKTPA
KTTKKETTTNPTKKPTLTTTERDTSTSQSTVLDTTTLEHTIQQQSLHSTTPENTPNSTQTPTASEPSTSNSTQNTQS
HA

What is claimed is:

1. An immunogenic composition comprising an immune stimulant and an RSV oligopeptide comprising an amino acid sequence set forth as SEQ ID NO: 29, wherein the RSV oligopeptide is less than 50 amino acids in length, and wherein the immune stimulant is in an amount effective to stimulate an immune response to the RSV oligopeptide.

2. The immunogenic composition of claim 1, further comprising a second immunogen.

3. The immunogenic composition of claim 2, wherein the second immunogen is from RSV.

4. The immunogenic composition of claim 2, wherein the second immunogen is from a virus other than RSV.

5. A method of inducing an immune response against respiratory syncytial virus (RSV) infection in a subject, the method comprising administering to the subject an immunologically effective amount of the immunogenic composition of claim 1.

6. The method of claim 5, wherein the immunogenic composition is administered intramuscularly.

7. The method of claim 5, wherein the subject is an infant.

* * * * *

SEQUENCE LISTING

<160> NUMBER OF SEQ ID NOS: 42

<210> SEQ ID NO 1
<211> LENGTH: 696
<212> TYPE: DNA
<213> ORGANISM: Artificial Sequence -continued

```
<220> FEATURE:
<223> OTHER INFORMATION: Synthetic RSV-A2 ectodomain (67-298) codon
      optimized sequence for E. coli

<400> SEQUENCE: 1
cataaagtca ccccgaccac ggcgattatc caggatgcca cctctcaaat caaaaacacc     60
acgccgacgt acctgaccca gaatccgcaa ctgggcattt caccgtcgaa cccgtcagaa    120
atcacctcgc agattaccac gatcctggca agcaccacgc cgggtgtcaa aagcacgctg    180
caatctacca cggtgaaaac caaaaatacc acgaccacgc agacccaacc gagcaaaccg    240
accacgaaac agcgtcaaaa taaaccgccg tctaaaccga acaatgattt tcacttcgaa    300
gtgtttaact tcgttccgtg cagtatttgt tccaacaatc cgacctgctg ggccatttgt    360
aaacgcatcc cgaacaaaaa accgggcaag aaaaccacga ccaaaccgac gaaaaaaccg    420
accctgaaaa cgaccaaaaa agacccgaaa ccgcagacga ccaaaagcaa agaagtgccg    480
acgaccaaac cgacggaaga accgaccatt aacacgacca aaaccaatat tatcacgacc    540
ctgctgacct ccaacacgac cggcaatccg gaactgacct cacagatgga aacgttccat    600
tcgaccagct ctgaaggtaa tccgagcccg tctcaggtca gcacgacctc cgaatacccg    660
agccagccgt cttctccgcc gaatacccg cgtcag                               696

<210> SEQ ID NO 2
<211> LENGTH: 232
<212> TYPE: PRT
<213> ORGANISM: Artificial Sequence
<220> FEATURE:
<223> OTHER INFORMATION: Synthetic RSV-A2 ectodomain (67-298) protein

<400> SEQUENCE: 2

His Lys Val Thr Pro Thr Thr Ala Ile Ile Gln Asp Ala Thr Ser Gln
1               5                   10                  15

Ile Lys Asn Thr Thr Pro Thr Tyr Leu Thr Gln Asn Pro Gln Leu Gly
            20                  25                  30

Ile Ser Pro Ser Asn Pro Ser Glu Ile Thr Ser Gln Ile Thr Thr Ile
        35                  40                  45

Leu Ala Ser Thr Thr Pro Gly Val Lys Ser Thr Leu Gln Ser Thr Thr
    50                  55                  60

Val Lys Thr Lys Asn Thr Thr Thr Thr Gln Thr Gln Pro Ser Lys Pro
65                  70                  75                  80

Thr Thr Lys Gln Arg Gln Asn Lys Pro Pro Ser Lys Pro Asn Asn Asp
                85                  90                  95

Phe His Phe Glu Val Phe Asn Phe Val Pro Cys Ser Ile Cys Ser Asn
            100                 105                 110

Asn Pro Thr Cys Trp Ala Ile Cys Lys Arg Ile Pro Asn Lys Lys Pro
        115                 120                 125

Gly Lys Lys Thr Thr Thr Lys Pro Thr Lys Lys Pro Thr Leu Lys Thr
    130                 135                 140

Thr Lys Lys Asp Pro Lys Pro Gln Thr Thr Lys Ser Lys Glu Val Pro
145                 150                 155                 160

Thr Thr Lys Pro Thr Glu Glu Pro Thr Ile Asn Thr Thr Lys Thr Asn
                165                 170                 175

Ile Ile Thr Thr Leu Leu Thr Ser Asn Thr Thr Gly Asn Pro Glu Leu
            180                 185                 190

Thr Ser Gln Met Glu Thr Phe His Ser Thr Ser Ser Glu Gly Asn Pro
        195                 200                 205
```

```
Ser Pro Ser Gln Val Ser Thr Thr Ser Glu Tyr Pro Ser Gln Pro Ser
    210                 215                 220

Ser Pro Pro Asn Thr Pro Arg Gln
225                 230

<210> SEQ ID NO 3
<211> LENGTH: 34
<212> TYPE: PRT
<213> ORGANISM: Artificial Sequence
<220> FEATURE:
<223> OTHER INFORMATION: Synthetic RSV-F peptide (amino acids 1-34)

<400> SEQUENCE: 3

Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln

<210> SEQ ID NO 4
<211> LENGTH: 52
<212> TYPE: PRT
<213> ORGANISM: Artificial Sequence
<220> FEATURE:
<223> OTHER INFORMATION: Synthetic RSV-F peptide (amino acids 23-74)

<400> SEQUENCE: 4

Ala Ser Gly Gln Asn Ile Thr Glu Glu Phe Tyr Gln Ser Thr Cys Ser
1               5                   10                  15

Ala Val Ser Lys Gly Tyr Leu Ser Ala Leu Arg Thr Gly Trp Tyr Thr
            20                  25                  30

Ser Val Ile Thr Ile Glu Leu Ser Asn Ile Lys Lys Asn Lys Cys Asn
        35                  40                  45

Gly Thr Asp Ala
    50

<210> SEQ ID NO 5
<211> LENGTH: 57
<212> TYPE: PRT
<213> ORGANISM: Artificial Sequence
<220> FEATURE:
<223> OTHER INFORMATION: Synthetic RSV-F peptide (amino acids 101-157)

<400> SEQUENCE: 5

Pro Ala Thr Asn Asn Arg Ala Arg Arg Glu Leu Pro Arg Phe Met Asn
1               5                   10                  15

Tyr Thr Leu Asn Asn Ala Lys Lys Thr Asn Val Thr Leu Ser Lys Lys
            20                  25                  30

Arg Lys Arg Arg Phe Leu Gly Phe Leu Leu Gly Val Gly Ser Ala Ile
        35                  40                  45

Ala Ser Gly Val Ala Val Ser Lys Val
    50                  55

<210> SEQ ID NO 6
<211> LENGTH: 34
<212> TYPE: PRT
<213> ORGANISM: Artificial Sequence
<220> FEATURE:
<223> OTHER INFORMATION: Synthetic RSV-F peptide (amino acids 82-115)

<400> SEQUENCE: 6

Glu Leu Asp Lys Tyr Lys Asn Ala Val Thr Glu Leu Gln Leu Leu Met
```

```
                1               5                  10                  15
Gln Ser Thr Pro Ala Thr Asn Asn Arg Ala Arg Arg Glu Leu Pro Arg
                20                  25                  30
Phe Met

<210> SEQ ID NO 7
<211> LENGTH: 21
<212> TYPE: PRT
<213> ORGANISM: Artificial Sequence
<220> FEATURE:
<223> OTHER INFORMATION: Synthetic RSV-F peptide (amino acids 101-121)

<400> SEQUENCE: 7

Pro Ala Thr Asn Asn Arg Ala Arg Arg Glu Leu Pro Arg Phe Met Asn
1               5                   10                  15

Tyr Thr Leu Asn Asn
                20

<210> SEQ ID NO 8
<211> LENGTH: 19
<212> TYPE: PRT
<213> ORGANISM: Artificial Sequence
<220> FEATURE:
<223> OTHER INFORMATION: Synthetic RSV-F peptide (amino acids 137-155)

<400> SEQUENCE: 8

Phe Leu Gly Phe Leu Leu Gly Val Gly Ser Ala Ile Ala Ser Gly Val
1               5                   10                  15

Ala Val Ser

<210> SEQ ID NO 9
<211> LENGTH: 30
<212> TYPE: PRT
<213> ORGANISM: Artificial Sequence
<220> FEATURE:
<223> OTHER INFORMATION: Synthetic RSV-F peptide (amino acids 174-203)

<400> SEQUENCE: 9

Thr Asn Lys Ala Val Val Ser Leu Ser Asn Gly Val Ser Val Leu Thr
1               5                   10                  15

Ser Lys Val Leu Asp Leu Lys Asn Tyr Ile Asp Lys Gln Leu
                20                  25                  30

<210> SEQ ID NO 10
<211> LENGTH: 65
<212> TYPE: PRT
<213> ORGANISM: Artificial Sequence
<220> FEATURE:
<223> OTHER INFORMATION: Synthetic RSV-F peptide (amino acids 176-240)

<400> SEQUENCE: 10

Lys Ala Val Val Ser Leu Ser Asn Gly Val Ser Val Leu Thr Ser Lys
1               5                   10                  15

Val Leu Asp Leu Lys Asn Tyr Ile Asp Lys Gln Leu Leu Pro Ile Val
                20                  25                  30

Asn Lys Gln Ser Cys Ser Ile Ser Asn Ile Glu Thr Val Ile Glu Phe
                35                  40                  45

Gln Gln Lys Asn Asn Arg Leu Leu Glu Ile Thr Arg Glu Phe Ser Val
        50                  55                  60

Asn
65
```

<210> SEQ ID NO 11
<211> LENGTH: 44
<212> TYPE: PRT
<213> ORGANISM: Artificial Sequence
<220> FEATURE:
<223> OTHER INFORMATION: Synthetic RSV-F peptide (amino acids 190-233)

<400> SEQUENCE: 11

Ser Lys Val Leu Asp Leu Lys Asn Tyr Ile Asp Lys Gln Leu Leu Pro
1               5                   10                  15

Ile Val Asn Lys Gln Ser Cys Ser Ile Ser Asn Ile Glu Thr Val Ile
            20                  25                  30

Glu Phe Gln Gln Lys Asn Asn Arg Leu Leu Glu Ile
        35                  40

<210> SEQ ID NO 12
<211> LENGTH: 46
<212> TYPE: PRT
<213> ORGANISM: Artificial Sequence
<220> FEATURE:
<223> OTHER INFORMATION: Synthetic RSV-F peptide (amino acids 195-240)

<400> SEQUENCE: 12

Leu Lys Asn Tyr Ile Asp Lys Gln Leu Leu Pro Ile Val Asn Lys Gln
1               5                   10                  15

Ser Cys Ser Ile Ser Asn Ile Glu Thr Val Ile Glu Phe Gln Gln Lys
            20                  25                  30

Asn Asn Arg Leu Leu Glu Ile Thr Arg Glu Phe Ser Val Asn
        35                  40                  45

<210> SEQ ID NO 13
<211> LENGTH: 29
<212> TYPE: PRT
<213> ORGANISM: Artificial Sequence
<220> FEATURE:
<223> OTHER INFORMATION: Synthetic RSV-F peptide (amino acids 216-244)

<400> SEQUENCE: 13

Asn Ile Glu Thr Val Ile Glu Phe Gln Gln Lys Asn Asn Arg Leu Leu
1               5                   10                  15

Glu Ile Thr Arg Glu Phe Ser Val Asn Ala Gly Val Thr
            20                  25

<210> SEQ ID NO 14
<211> LENGTH: 54
<212> TYPE: PRT
<213> ORGANISM: Artificial Sequence
<220> FEATURE:
<223> OTHER INFORMATION: Synthetic RSV-F peptide (amino acids 234-287)

<400> SEQUENCE: 14

Thr Arg Glu Phe Ser Val Asn Ala Gly Val Thr Thr Pro Val Ser Thr
1               5                   10                  15

Tyr Met Leu Thr Asn Ser Glu Leu Leu Ser Leu Ile Asn Asp Met Pro
            20                  25                  30

Ile Thr Asn Asp Gln Lys Lys Leu Met Ser Asn Asn Val Gln Ile Val
        35                  40                  45

Arg Gln Gln Ser Tyr Ser
    50

<210> SEQ ID NO 15
<211> LENGTH: 24

```
<212> TYPE: PRT
<213> ORGANISM: Artificial Sequence
<220> FEATURE:
<223> OTHER INFORMATION: Synthetic RSV-F peptide (amino acids 250-273)

<400> SEQUENCE: 15

Tyr Met Leu Thr Asn Ser Glu Leu Leu Ser Leu Ile Asn Asp Met Pro
1               5                   10                  15

Ile Thr Asn Asp Gln Lys Lys Leu
            20

<210> SEQ ID NO 16
<211> LENGTH: 59
<212> TYPE: PRT
<213> ORGANISM: Artificial Sequence
<220> FEATURE:
<223> OTHER INFORMATION: Synthetic RSV-F peptide (amino acids 310-368)

<400> SEQUENCE: 16

Asp Thr Pro Cys Trp Lys Leu His Thr Ser Pro Leu Cys Thr Thr Asn
1               5                   10                  15

Thr Lys Glu Gly Ser Asn Ile Cys Leu Thr Arg Thr Asp Arg Gly Trp
            20                  25                  30

Tyr Cys Asp Asn Ala Gly Ser Val Ser Phe Phe Pro Gln Ala Glu Thr
        35                  40                  45

Cys Lys Val Gln Ser Asn Arg Val Phe Cys Asp
    50                  55

<210> SEQ ID NO 17
<211> LENGTH: 18
<212> TYPE: PRT
<213> ORGANISM: Artificial Sequence
<220> FEATURE:
<223> OTHER INFORMATION: Synthetic RSV-F peptide (amino acids 341-358)

<400> SEQUENCE: 17

Trp Tyr Cys Asp Asn Ala Gly Ser Val Ser Phe Phe Pro Gln Ala Glu
1               5                   10                  15

Thr Cys

<210> SEQ ID NO 18
<211> LENGTH: 30
<212> TYPE: PRT
<213> ORGANISM: Artificial Sequence
<220> FEATURE:
<223> OTHER INFORMATION: Synthetic RSV-F peptide (amino acids 425-450)

<400> SEQUENCE: 18

Asn Ser Leu Thr Leu Pro Ser Glu Val Asn Leu Cys Asn Val Asp Ile
1               5                   10                  15

Phe Asn Pro Lys Tyr Asp Cys Lys Ile Met Thr Ser Lys Thr
            20                  25                  30

<210> SEQ ID NO 19
<211> LENGTH: 26
<212> TYPE: PRT
<213> ORGANISM: Artificial Sequence
<220> FEATURE:
<223> OTHER INFORMATION: Synthetic RSV-F peptide (amino acids 425-450)

<400> SEQUENCE: 19

Ser Asn Lys Asn Arg Gly Ile Ile Lys Thr Phe Ser Asn Gly Cys Asp
1               5                   10                  15
```

Tyr Val Ser Asn Lys Gly Val Asp Thr Val
            20                  25

<210> SEQ ID NO 20
<211> LENGTH: 19
<212> TYPE: PRT
<213> ORGANISM: Artificial Sequence
<220> FEATURE:
<223> OTHER INFORMATION: Synthetic RSV-F peptide (amino acids 443-461)

<400> SEQUENCE: 20

Ser Asn Lys Gly Val Asp Thr Val Ser Val Gly Asn Thr Leu Tyr Tyr
1               5                   10                  15

Val Asn Lys

<210> SEQ ID NO 21
<211> LENGTH: 47
<212> TYPE: PRT
<213> ORGANISM: Artificial Sequence
<220> FEATURE:
<223> OTHER INFORMATION: Synthetic RSV-F peptide (amino acids 475-521)

<400> SEQUENCE: 21

Ile Asn Phe Tyr Asp Pro Leu Val Phe Pro Ser Asp Glu Phe Asp Ala
1               5                   10                  15

Ser Ile Ser Gln Val Asn Glu Lys Ile Asn Gln Ser Leu Ala Phe Ile
            20                  25                  30

Arg Lys Ser Asp Glu Leu Leu His Asn Val Asn Ala Val Lys Ser
        35                  40                  45

<210> SEQ ID NO 22
<211> LENGTH: 23
<212> TYPE: PRT
<213> ORGANISM: Artificial Sequence
<220> FEATURE:
<223> OTHER INFORMATION: Synthetic RSV-F peptide (amino acids 471-493)

<400> SEQUENCE: 22

Gly Glu Pro Ile Ile Asn Phe Tyr Asp Pro Leu Val Phe Pro Ser Asp
1               5                   10                  15

Glu Phe Asp Ala Ser Ile Ser
            20

<210> SEQ ID NO 23
<211> LENGTH: 25
<212> TYPE: PRT
<213> ORGANISM: Artificial Sequence
<220> FEATURE:
<223> OTHER INFORMATION: Synthetic RSV-F peptide (amino acids 497-521)

<400> SEQUENCE: 23

Glu Lys Ile Asn Gln Ser Leu Ala Phe Ile Arg Lys Ser Asp Glu Leu
1               5                   10                  15

Leu His Asn Val Asn Ala Val Lys Ser
            20                  25

<210> SEQ ID NO 24
<211> LENGTH: 21
<212> TYPE: PRT
<213> ORGANISM: Artificial Sequence
<220> FEATURE:
<223> OTHER INFORMATION: Synthetic RSV-F peptide (amino acids 552-572)

<400> SEQUENCE: 24

Ala Arg Ser Thr Pro Val Thr Leu Ser Lys Asp Gln Leu Ser Gly Ile
1               5                   10                  15

Asn Asn Ile Ala Phe
            20

<210> SEQ ID NO 25
<211> LENGTH: 29
<212> TYPE: PRT
<213> ORGANISM: Artificial Sequence
<220> FEATURE:
<223> OTHER INFORMATION: Synthetic RSV-G peptide (amino acids 33-61)

<400> SEQUENCE: 25

Leu Asn Leu Lys Ser Val Ala Gln Ile Thr Leu Ser Ile Leu Ala Met
1               5                   10                  15

Ile Ile Ser Thr Ser Leu Ile Ile Ala Ala Ile Ile Phe
            20                  25

<210> SEQ ID NO 26
<211> LENGTH: 25
<212> TYPE: PRT
<213> ORGANISM: Artificial Sequence
<220> FEATURE:
<223> OTHER INFORMATION: Synthetic RSV-G peptide (amino acids 66-90)

<400> SEQUENCE: 26

Asn His Lys Val Thr Pro Thr Thr Ala Ile Ile Gln Asp Ala Thr Ser
1               5                   10                  15

Gln Ile Lys Asn Thr Thr Pro Thr Tyr
            20                  25

<210> SEQ ID NO 27
<211> LENGTH: 21
<212> TYPE: PRT
<213> ORGANISM: Artificial Sequence
<220> FEATURE:
<223> OTHER INFORMATION: Synthetic RSV-G peptide (amino acids 90-110)

<400> SEQUENCE: 27

Tyr Leu Thr Gln Asn Pro Gln Leu Gly Ile Ser Pro Ser Asn Pro Ser
1               5                   10                  15

Glu Ile Thr Ser Gln
            20

<210> SEQ ID NO 28
<211> LENGTH: 24
<212> TYPE: PRT
<213> ORGANISM: Artificial Sequence
<220> FEATURE:
<223> OTHER INFORMATION: Synthetic RSV-G peptide (amino acids 129-152)

<400> SEQUENCE: 28

Thr Thr Val Lys Thr Lys Asn Thr Thr Thr Thr Gln Thr Gln Pro Ser
1               5                   10                  15

Lys Pro Thr Thr Lys Gln Arg Gln
            20

<210> SEQ ID NO 29
<211> LENGTH: 31
<212> TYPE: PRT
<213> ORGANISM: Artificial Sequence
<220> FEATURE:
<223> OTHER INFORMATION: Synthetic RSV-G peptide (amino acids 148-178)

<400> SEQUENCE: 29

```
Thr Thr Lys Gln Arg Gln Asn Lys Pro Pro Ser Lys Pro Asn Asn Asp
1               5                   10                  15

Phe His Phe Glu Val Phe Asn Phe Val Pro Cys Ser Ile Cys Ser
                20                  25                  30

<210> SEQ ID NO 30
<211> LENGTH: 39
<212> TYPE: PRT
<213> ORGANISM: Artificial Sequence
<220> FEATURE:
<223> OTHER INFORMATION: Synthetic RSV-G peptide (amino acids 169-207)

<400> SEQUENCE: 30

Asn Phe Val Pro Cys Ser Ile Cys Ser Asn Asn Pro Thr Cys Trp Ala
1               5                   10                  15

Ile Cys Lys Arg Ile Pro Asn Lys Lys Pro Gly Lys Lys Thr Thr Thr
                20                  25                  30

Lys Pro Thr Lys Lys Pro Thr
            35

<210> SEQ ID NO 31
<211> LENGTH: 28
<212> TYPE: PRT
<213> ORGANISM: Artificial Sequence
<220> FEATURE:
<223> OTHER INFORMATION: Synthetic RSV-G peptide (amino acids 236-263)

<400> SEQUENCE: 31

Ile Asn Thr Thr Lys Thr Asn Ile Ile Thr Thr Leu Leu Thr Ser Asn
1               5                   10                  15

Thr Thr Gly Asn Pro Glu Leu Thr Ser Gln Met Glu
                20                  25

<210> SEQ ID NO 32
<211> LENGTH: 30
<212> TYPE: PRT
<213> ORGANISM: Artificial Sequence
<220> FEATURE:
<223> OTHER INFORMATION: Synthetic RSV-G peptide (amino acids 245-274)

<400> SEQUENCE: 32

Thr Thr Leu Leu Thr Ser Asn Thr Thr Gly Asn Pro Glu Leu Thr Ser
1               5                   10                  15

Gln Met Glu Thr Phe His Ser Thr Ser Ser Glu Gly Asn Pro
                20                  25                  30

<210> SEQ ID NO 33
<211> LENGTH: 34
<212> TYPE: PRT
<213> ORGANISM: Artificial Sequence
<220> FEATURE:
<223> OTHER INFORMATION: Synthetic RSV-G peptide (amino acids 263-298)

<400> SEQUENCE: 33

Glu Thr Phe His Ser Thr Ser Ser Glu Gly Asn Pro Ser Pro Ser Gln
1               5                   10                  15

Val Ser Thr Thr Ser Glu Tyr Pro Ser Gln Pro Ser Ser Pro Pro Asn
                20                  25                  30

Thr Pro

<210> SEQ ID NO 34
<211> LENGTH: 298
```

```
<212> TYPE: PRT
<213> ORGANISM: Human respiratory syncytial virus

<400> SEQUENCE: 34

Met Ser Lys Asn Lys Asp Gln Arg Thr Ala Lys

```
Ile Ile Ser Thr Ser Leu Ile Ile Thr Ala Ile Ile Phe Ile Ala Ser
 50                  55                  60

Ala Asn His Lys Val Thr Leu Thr Thr Ala Ile Ile Gln Asp Ala Thr
 65                  70                  75                  80

Ser Gln Ile Lys Asn Thr Thr Pro Thr Tyr Leu Thr Gln Asp Pro Gln
                 85                  90                  95

Leu Gly Ile Ser Phe Ser Asn Leu Ser Glu Ile Thr Ser Gln Thr Thr
                100                 105                 110

Thr Ile Leu Ala Ser Thr Thr Pro Gly Val Lys Ser Asn Leu Gln Pro
        115                 120                 125

Thr Thr Val Lys Thr Lys Asn Thr Thr Thr Thr Gln Thr Gln Pro Ser
    130                 135                 140

Lys Pro Thr Thr Lys Gln Arg Gln Asn Lys Pro Pro Asn Lys Pro Asn
145                 150                 155                 160

Asn Asp Phe His Phe Glu Val Phe Asn Phe Val Pro Cys Ser Ile Cys
                165                 170                 175

Ser Asn Asn Pro Thr Cys Trp Ala Ile Cys Lys Arg Ile Pro Asn Lys
                180                 185                 190

Lys Pro Gly Lys Lys Thr Thr Thr Lys Pro Thr Lys Lys Pro Thr Phe
            195                 200                 205

Lys Thr Thr Lys Lys Asp His Lys Pro Gln Thr Thr Lys Pro Lys Glu
    210                 215                 220

Val Pro Thr Thr Lys Pro Thr Glu Glu Pro Thr Ile Asn Thr Thr Lys
225                 230                 235                 240

Thr Asn Ile Ile Thr Thr Leu Leu Thr Asn Asn Thr Thr Gly Asn Pro
                245                 250                 255

Lys Leu Thr Ser Gln Met Glu Thr Phe His Ser Thr Ser Ser Glu Gly
                260                 265                 270

Asn Leu Ser Pro Ser Gln Val Ser Thr Thr Ser Glu His Pro Ser Gln
            275                 280                 285

Pro Ser Ser Pro Pro Asn Thr Thr Arg Gln
        290                 295
```

<210> SEQ ID NO 36
<211> LENGTH: 292
<212> TYPE: PRT
<213> ORGANISM: Human respiratory syncytial virus

<400> SEQUENCE: 36

```
Met Ser Lys His Lys Asn Gln Arg Thr Ala Arg Thr Leu Glu Lys Thr
 1               5                  10                  15

Trp Asp Thr Leu Asn His Leu Ile Val Ile Ser Ser Cys Leu Tyr Arg
                 20                  25                  30

Leu Asn Leu Lys Ser Ile Ala Gln Ile Ala Leu Ser Val Leu Ala Met
            35                  40                  45

Ile Ile Ser Thr Ser Leu Ile Ile Ala Ala Ile Phe Ile Ile Ser
 50                  55                  60

Ala Asn His Lys Val Thr Leu Thr Thr Val Thr Val Gln Thr Ile Lys
 65                  70                  75                  80

Asn His Thr Glu Lys Asn Ile Ser Thr Tyr Leu Thr Gln Val Pro Pro
                 85                  90                  95

Glu Arg Val Asn Ser Ser Lys Gln Pro Thr Thr Thr Ser Pro Ile His
                100                 105                 110

Thr Asn Ser Ala Thr Ile Ser Pro Asn Thr Lys Ser Glu Thr His His
            115                 120                 125
```

-continued

Thr Thr Ala Gln Thr Lys Gly Arg Ile Thr Thr Ser Thr Gln Thr Asn
            130                 135                 140

Lys Pro Ser Thr Lys Ser Arg Ser Lys Asn Pro Pro Lys Lys Pro Lys
145                 150                 155                 160

Asp Asp Tyr His Phe Glu Val Phe Asn Phe Val Pro Cys Ser Ile Cys
                165                 170                 175

Gly Asn Asn Gln Leu Cys Lys Ser Ile Cys Lys Thr Ile Pro Ser Asn
            180                 185                 190

Lys Pro Lys Lys Lys Pro Thr Ile Lys Pro Thr Asn Lys Pro Thr Thr
            195                 200                 205

Lys Thr Thr Asn Lys Arg Asp Pro Lys Thr Pro Ala Lys Met Pro Lys
            210                 215                 220

Lys Glu Ile Ile Thr Asn Pro Ala Lys Lys Pro Thr Leu Lys Thr Thr
225                 230                 235                 240

Glu Arg Asp Thr Ser Ile Ser Gln Ser Thr Val Leu Asp Thr Ile Thr
                245                 250                 255

Pro Lys Tyr Thr Ile Gln Gln Gln Ser Leu His Ser Thr Thr Ser Glu
                260                 265                 270

Asn Thr Pro Ser Ser Thr Gln Ile Pro Thr Ala Ser Glu Pro Ser Thr
            275                 280                 285

Leu Asn Pro Asn
    290

<210> SEQ ID NO 37
<211> LENGTH: 299
<212> TYPE: PRT
<213> ORGANISM: Human respiratory syncytial virus

<400> SEQUENCE: 37

Met Ser Lys His Lys Asn Gln Arg Thr Ala Arg Thr Leu Gl

|   | 195 |   |   |   | 200 |   |   |   | 205 |   |   |
|---|---|---|---|---|---|---|---|---|---|---|---|
| Lys | Thr | Thr | Asn | Lys | Arg | Asp | Pro | Lys | Thr | Pro | Ala | Lys | Thr | Thr | Lys |
|   |   | 210 |   |   |   |   | 215 |   |   |   |   | 220 |   |   |   |

Lys Thr Thr Asn Lys Arg Asp Pro Lys Thr Pro Ala Lys Thr Thr Lys
        210              215              220

Lys Glu Thr Thr Thr Asn Pro Thr Lys Lys Pro Thr Leu Thr Thr Thr
225              230              235              240

Glu Arg Asp Thr Ser Thr Ser Gln Ser Thr Val Leu Asp Thr Thr Thr
            245              250              255

Leu Glu His Thr Ile Gln Gln Ser Leu His Ser Thr Thr Pro Glu
        260              265              270

Asn Thr Pro Asn Ser Thr Gln Thr Pro Thr Ala Ser Glu Pro Ser Thr
        275              280              285

Ser Asn Ser Thr Gln Asn Thr Gln Ser His Ala
        290              295

<210> SEQ ID NO 38
<211> LENGTH: 1722
<212> TYPE: DNA
<213> ORGANISM: Artificial Sequence
<220> FEATURE:
<223> OTHER INFORMATION: Synthetic RSV-A2 F codon optimized sequence for
    E. coli

<400> SEQUENCE: 38

```
atggaactgc tgattctgaa agccaacgca attaccacga ttctgaccgc tgttaccttc      60
tgtttcgcct cgggccaaaa tatcacggaa gaattttatc agagtacctg ctccgcagtt     120
tcaaaaggct atctgagcgc tctgcgtacc ggttggtaca cgtcggtgat caccattgaa     180
ctgagcaaca ttaaaagaa caagtgtaat ggcacggatg ccaaaatcaa gctgattaaa     240
caggaactgg acaagtacaa gaacgcagtt accgaactgc agctgctgat gcaaagcacc     300
ccggcaacga acaatcgtgc tcgtcgcgaa ctgccgcgct tcatgaacta cacccctgaac     360
aatgctaaaa agaccaatgt tacgctgtcc aaaaagcgca acgtcgctt tctgggcttc     420
ctgctgggtg tgggtagcgc cattgccagc ggcgttgcag tctctaaagt gctgcatctg     480
gaaggtgaag ttaacaaaat caagtctgcg ctgctgagta cgaacaaagc cgtggttttcc     540
ctgtcaaatg gtgtgtccgt tctgacctca aaagtgctgg atctgaagaa ttatatcgac     600
aaacagctgc tgccgattgt gaacaagcaa tcgtgcagca tctctaacat cgaaacggtt     660
atcgaattc agcagaaaaa caatcgtctg ctggaaatca cccgtgaatt ttcggttaac     720
gccggtgtca ccacgcctgt gagcacgtat atgctgacca attcggaact gctgagcctg     780
atcaacgata tgccgattac caatgaccag aaaaagctga tgtcgaacaa tgttcaaatt     840
gtccgtcagc aaagttactc catcatgagc attatcaaag aagaagttct ggcgtatgtc     900
gtgcagctgc cgctgtacgg cgtcattgat acgccgtgct ggaagctgca cacctctccg     960
ctgtgtacca cgaacaccaa agaaggtagt aatatttgcc tgacccgtac ggatcgcggc    1020
tggtattgtg acaacgcggg ttcagtttcg tttttccccgc aggccgaaac ctgcaaagtg    1080
caaagcaacc gtgtgttttg cgatacgatg aacagcctga ccctgccgag tgaagtcaac    1140
ctgtgcaatg tggatatttt caatccgaaa tacgactgta agatcatgac cagtaaaacg    1200
gatgttagct ctagtgtcat cacctccctg ggcgcgattg tgtcatgcta tggtaaaacc    1260
aagtgtacgg ccagcaacaa gaatcgcggc attatcaaaa cctttttctaa cggttgcgat    1320
tacgttagta ataaaggcgt cgacacggtc tctgtgggta cacccctgta ttacgtcaat    1380
aaacaggaag gcaagagtct gtatgtgaaa ggtgaaccga ttatcaactt ttacgatccg    1440
```

-continued

```
ctggtctttc cgtctgatga atttgacgca agcatctctc aggtgaacga aaagattaat    1500
caatccctgg ctttcatccg taaatcagac gaactgctgc ataacgtgaa tgcggttaaa    1560
agcaccacga atatcatgat taccacgatt atcattgtca tcattgtgat cctgctgtcc    1620
ctgattgcag tgggcctgct gctgtattgt aaagctcgct caacgccggt gacgctgagc    1680
aaagaccaac tgtcgggtat caataacatc gcatttagca ac                      1722
```

<210> SEQ ID NO 39
<211> LENGTH: 574
<212> TYPE: PRT
<213> ORGANISM: Artificial Sequence
<220> FEATURE:
<223> OTHER INFORMATION: Synthetic RSV-A2 F protein sequence

<400> SEQUENCE: 39

```
Met Glu Leu Leu Ile Leu Lys Ala Asn Ala Ile Thr Thr Ile Leu Thr
1               5                   10                  15

Ala Val Thr Phe Cys Phe Ala Ser Gly Gln Asn Ile Thr Glu Glu Phe
            20                  25                  30

Tyr Gln Ser Thr Cys Ser Ala Val Ser Lys Gly Tyr Leu Ser Ala Leu
        35                  40                  45

Arg Thr Gly Trp Tyr Thr Ser Val Ile Thr Ile Glu Leu Ser Asn Ile
    50                  55                  60

Lys Lys Asn Lys Cys Asn Gly Thr Asp Ala Lys Ile Lys Leu Ile Lys
65                  70                  75                  80

Gln Glu Leu Asp Lys Tyr Lys Asn Ala Val Thr Glu Leu Gln Leu Leu
                85                  90                  95

Met Gln Ser Thr Pro Ala Thr Asn Asn Arg Ala Arg Arg Glu Leu Pro
            100                 105                 110

Arg Phe Met Asn Tyr Thr Leu Asn Asn Ala Lys Lys Thr Asn Val Thr
        115                 120                 125

Leu Ser Lys Lys Arg Lys Arg Arg Phe Leu Gly Phe Leu Leu Gly Val
    130                 135                 140

Gly Ser Ala Ile Ala Ser Gly Val Ala Val Ser Lys Val Leu His Leu
145                 150                 155                 160

Glu Gly Glu Val Asn Lys Ile Lys Ser Ala Leu Leu Ser Thr Asn Lys
                165                 170                 175

Ala Val Val Ser Leu Ser Asn Gly Val Ser Val Leu Thr Ser Lys Val
            180                 185                 190

Leu Asp Leu Lys Asn Tyr Ile Asp Lys Gln Leu Leu Pro Ile Val Asn
        195                 200                 205

Lys Gln Ser Cys Ser Ile Ser Asn Ile Glu Thr Val Ile Glu Phe Gln
    210                 215                 220

Gln Lys Asn Asn Arg Leu Leu Glu Ile Thr Arg Glu Phe Ser Val Asn
225                 230                 235                 240

Ala Gly Val Thr Thr Pro Val Ser Thr Tyr Met Leu Thr Asn Ser Glu
                245                 250                 255

Leu Leu Ser Leu Ile Asn Asp Met Pro Ile Thr Asn Asp Gln Lys Lys
            260                 265                 270

Leu Met Ser Asn Asn Val Gln Ile Val Arg Gln Gln Ser Tyr Ser Ile
        275                 280                 285

Met Ser Ile Ile Lys Glu Glu Val Leu Ala Tyr Val Val Gln Leu Pro
    290                 295                 300

Leu Tyr Gly Val Ile Asp Thr Pro Cys Trp Lys Leu His Thr Ser Pro
305                 310                 315                 320
```

```
Leu Cys Thr Thr Asn Thr Lys Glu Gly Ser Asn Ile Cys Leu Thr Arg
                325                 330                 335

Thr Asp Arg Gly Trp Tyr Cys Asp Asn Ala Gly Ser Val Ser Phe Phe
            340                 345                 350

Pro Gln Ala Glu Thr Cys Lys Val Gln Ser Asn Arg Val Phe Cys Asp
        355                 360                 365

Thr Met Asn Ser Leu Thr Leu Pro Ser Glu Val Asn Leu Cys Asn Val
370                 375                 380

Asp Ile Phe Asn Pro Lys Tyr Asp Cys Lys Ile Met Thr Ser Lys Thr
385                 390                 395                 400

Asp Val Ser Ser Ser Val Ile Thr Ser Leu Gly Ala Ile Val Ser Cys
            405                 410                 415

Tyr Gly Lys Thr Lys Cys Thr Ala Ser Asn Lys Asn Arg Gly Ile Ile
        420                 425                 430

Lys Thr Phe Ser Asn Gly Cys Asp Tyr Val Ser Asn Lys Gly Val Asp
    435                 440                 445

Thr Val Ser Val Gly Asn Thr Leu Tyr Tyr Val Asn Lys Gln Glu Gly
450                 455                 460

Lys Ser Leu Tyr Val Lys Gly Glu Pro Ile Ile Asn Phe Tyr Asp Pro
465                 470                 475                 480

Leu Val Phe Pro Ser Asp Glu Phe Asp Ala Ser Ile Ser Gln Val Asn
            485                 490                 495

Glu Lys Ile Asn Gln Ser Leu Ala Phe Ile Arg Lys Ser Asp Glu Leu
        500                 505                 510

Leu His Asn Val Asn Ala Val Lys Ser Thr Thr Asn Ile Met Ile Thr
    515                 520                 525

Thr Ile Ile Ile Val Ile Ile Val Ile Leu Leu Ser Leu Ile Ala Val
530                 535                 540

Gly Leu Leu Leu Tyr Cys Lys Ala Arg Ser Thr Pro Val Thr Leu Ser
545                 550                 555                 560

Lys Asp Gln Leu Ser Gly Ile Asn Asn Ile Ala Phe Ser Asn
            565                 570

<210> SEQ ID NO 40
<211> LENGTH: 502
<212> TYPE: PRT
<213> ORGANISM: Artificial Sequence
<220> FEATURE:
<223> OTHER INFORMATION: RSV-A2 F ectodomain (23-524) protein sequence

<400> SEQUENCE: 40

Ala Ser Gly Gln Asn Ile Thr Glu Glu Phe Tyr Gln Ser Thr Cys Ser
1               5                   10                  15

Ala Val Ser Lys Gly Tyr Leu Ser Ala Leu Arg Thr Gly Trp Tyr Thr
            20                  25                  30

Ser Val Ile Thr Ile Glu Leu Ser Asn Ile Lys Lys Asn Lys Cys Asn
        35                  40                  45

Gly Thr Asp Ala Lys Ile Lys Leu Ile Lys Gln Glu Leu Asp Lys Tyr
    50                  55                  60

Lys Asn Ala Val Thr Glu Leu Gln Leu Leu Met Gln Ser Thr Pro Ala
65                  70                  75                  80

Thr Asn Asn Arg Ala Arg Arg Glu Leu Pro Arg Phe Met Asn Tyr Thr
                85                  90                  95

Leu Asn Asn Ala Lys Lys Thr Asn Val Thr Leu Ser Lys Lys Arg Lys
            100                 105                 110
```

Arg Arg Phe Leu Gly Phe Leu Leu Gly Val Gly Ser Ala Ile Ala Ser
    115                 120                 125

Gly Val Ala Val Ser Lys Val Leu His Leu Glu Gly Glu Val Asn Lys
130                 135                 140

Ile Lys Ser Ala Leu Leu Ser Thr Asn Lys Ala Val Val Ser Leu Ser
145                 150                 155                 160

Asn Gly Val Ser Val Leu Thr Ser Lys Val Leu Asp Leu Lys Asn Tyr
                165                 170                 175

Ile Asp Lys Gln Leu Leu Pro Ile Val Asn Lys Gln Ser Cys Ser Ile
            180                 185                 190

Ser Asn Ile Glu Thr Val Ile Glu Phe Gln Gln Lys Asn Asn Arg Leu
        195                 200                 205

Leu Glu Ile Thr Arg Glu Phe Ser Val Asn Ala Gly Val Thr Thr Pro
    210                 215                 220

Val Ser Thr Tyr Met Leu Thr Asn Ser Glu Leu Leu Ser Leu Ile Asn
225                 230                 235                 240

Asp Met Pro Ile Thr Asn Asp Gln Lys Lys Leu Met Ser Asn Asn Val
                245                 250                 255

Gln Ile Val Arg Gln Gln Ser Tyr Ser Ile Met Ser Ile Ile Lys Glu
            260                 265                 270

Glu Val Leu Ala Tyr Val Val Gln Leu Pro Leu Tyr Gly Val Ile Asp
        275                 280                 285

Thr Pro Cys Trp Lys Leu His Thr Ser Pro Leu Cys Thr Thr Asn Thr
    290                 295                 300

Lys Glu Gly Ser Asn Ile Cys Leu Thr Arg Thr Asp Arg Gly Trp Tyr
305                 310                 315                 320

Cys Asp Asn Ala Gly Ser Val Ser Phe Phe Pro Gln Ala Glu Thr Cys
                325                 330                 335

Lys Val Gln Ser Asn Arg Val Phe Cys Asp Thr Met Asn Ser Leu Thr
            340                 345                 350

Leu Pro Ser Glu Val Asn Leu Cys Asn Val Asp Ile Phe Asn Pro Lys
        355                 360                 365

Tyr Asp Cys Lys Ile Met Thr Ser Lys Thr Asp Val Ser Ser Ser Val
    370                 375                 380

Ile Thr Ser Leu Gly Ala Ile Val Ser Cys Tyr Gly Lys Thr Lys Cys
385                 390                 395                 400

Thr Ala Ser Asn Lys Asn Arg Gly Ile Ile Lys Thr Phe Ser Asn Gly
                405                 410                 415

Cys Asp Tyr Val Ser Asn Lys Gly Val Asp Thr Val Ser Val Gly Asn
            420                 425                 430

Thr Leu Tyr Tyr Val Asn Lys Gln Glu Gly Lys Ser Leu Tyr Val Lys
        435                 440                 445

Gly Glu Pro Ile Ile Asn Phe Tyr Asp Pro Leu Val Phe Pro Ser Asp
    450                 455                 460

Glu Phe Asp Ala Ser Ile Ser Gln Val Asn Glu Lys Ile Asn Gln Ser
465                 470                 475                 480

Leu Ala Phe Ile Arg Lys Ser Asp Glu Leu Leu His Asn Val Asn Ala
                485                 490                 495

Val Lys Ser Thr Thr Asn
            500

<210> SEQ ID NO 41
<211> LENGTH: 699

<210> SEQ ID NO 41
<211> LENGTH: 699
<212> TYPE: DNA
<213> ORGANISM: Artificial Sequence
<220> FEATURE:
<223> OTHER INFORMATION: Synthetic RSV-B1 ectodomain (67-299) codon
      optimized sequence for E. coli

<400> SEQUENCE: 41

```
cataaagtta ccctgaccac ggtgacggtt cagaccatta aaaccacac cgagaaaaac      60
atcaccacgt acctgaccca agttccgccg aacgcgtca gctctagtaa acagccgacc     120
acgaccagcc cgattcatac caactcagcg acgacctcgc cgaatacgaa atctgaaacc    180
catcacacga ccgcccaaac caaaggccgt acgaccacga gtacgcagac caacaaaccg    240
tccaccaaac cgcgcctgaa aaatccgccg aaaaaaccga aagatgacta tcacttcgaa    300
gtctttaact tcgtgccgtg cagcatttgt ggtaacaatc agctgtgcaa atcaatttgt    360
aaaaccatcc cgtcgaataa accgaagaaa aaaccgacga tcaaaccgac caacaaaccg    420
accacgaaaa ccacgaataa acgtgatccg aaaaccccgg caaaaccac caagaaagaa    480
accacgacca cccgacgaa aaaaccgacc ctgacgacca cggaacgcga tacgtcgacc    540
agccaatcta ccgtcctgga caccacgacc ctggaacata ccattcagca acagagtctg    600
cactccacga ccccggaaaa cacgccgaat agcacccaga ccccgaccgc aagcgaaccg    660
agcaccagca actccacccca aaacacccaa tcccacgca                           699
```

<210> SEQ ID NO 42
<211> LENGTH: 233
<212> TYPE: PRT
<213> ORGANISM: Artificial Sequence
<220> FEATURE:
<223> OTHER INFORMATION: Synthetic RSV-B1 ectodomain (67-299) protein
      sequence

<400> SEQUENCE: 42

```
His Lys Val Thr Leu Thr Thr Val Thr Val Gln Thr Ile Lys Asn His
1               5                   10                  15

Thr Glu Lys Asn Ile Thr Thr Tyr Leu Thr Gln Val Pro Pro Glu Arg
            20                  25                  30

Val Ser Ser Ser Lys Gln Pro Thr Thr Thr Ser Pro Ile His Thr Asn
        35                  40                  45

Ser Ala Thr Thr Ser Pro Asn Thr Lys Ser Glu Thr His His Thr Thr
    50                  55                  60

Ala Gln Thr Lys Gly Arg Thr Thr Thr Ser Thr Gln Thr Asn Lys Pro
65                  70                  75                  80

Ser Thr Lys Pro Arg Leu Lys Asn Pro Pro Lys Lys Pro Lys Asp Asp
                85                  90                  95

Tyr His Phe Glu Val Phe Asn Phe Val Pro Cys Ser Ile Cys Gly Asn
            100                 105                 110

Asn Gln Leu Cys Lys Ser Ile Cys Lys Thr Ile Pro Ser Asn Lys Pro
        115                 120                 125

Lys Lys Lys Pro Thr Ile Lys Pro Thr Asn Lys Pro Thr Thr Lys Thr
    130                 135                 140

Thr Asn Lys Arg Asp Pro Lys Thr Pro Ala Lys Thr Thr Lys Lys Glu
145                 150                 155                 160

Thr Thr Thr Asn Pro Thr Lys Lys Pro Thr Leu Thr Thr Thr Glu Arg
                165                 170                 175

Asp Thr Ser Thr Ser Gln Ser Thr Val Leu Asp Thr Thr Thr Leu Glu
            180                 185                 190
```

-continued

```
His Thr Ile Gln Gln Gln Ser Leu His Ser Thr Thr Pro Glu Asn Thr
            195                 200                 205

Pro Asn Ser Thr Gln Thr Pro Thr Ala Ser Glu Pro Ser Thr Ser Asn
        210                 215                 220

Ser Thr Gln Asn Thr Gln Ser His Ala
225                 230
```